United States Patent [19]

Choi et al.

[11] 4,093,709

[45] June 6, 1978

[54] DRUG DELIVERY DEVICES MANUFACTURED FROM POLY(ORTHOESTERS) AND POLY(ORTHOCARBONATES)

[75] Inventors: Nam Sok Choi, Seoul, South Korea; Jorge Heller, Palo Alto, Calif.

[73] Assignee: Alza Corporation, Palo Alto, Calif.

[21] Appl. No.: 544,808

[22] Filed: Jan. 28, 1975

[51] Int. Cl.² .................... A61K 9/22; A61K 9/56; A61M 37/00

[52] U.S. Cl. ........................... 424/19; 424/20; 128/260

[58] Field of Search ............ 424/19, 20; 128/260, 128/268

[56] References Cited

U.S. PATENT DOCUMENTS

| | | | |
|---|---|---|---|
| 3,887,699 | 6/1975 | Yolles | 128/260 |
| 3,960,150 | 6/1977 | Hussain | 424/19 |
| 4,001,388 | 1/1977 | Shell | 424/19 |
| 4,014,987 | 3/1977 | Heller | 424/19 |

*Primary Examiner*—Henry R. Jiles
*Assistant Examiner*—Cary Owens

*Attorney, Agent, or Firm*—Paul L. Sabatine; Thomas E. Ciotti; Edward L. Mandell

[57] ABSTRACT

The invention concerns orthoester and orthocarbonate polymers having a repeating mer comprising a hydrocarbon radical and a symmetrical dioxycarbon unit of the general formula:

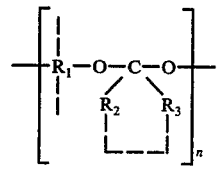

wherein $R_1$ is a multivalent hydrocarbon radical, $R_2$ and $R_3$ are hydrocarbon radicals with at least one of $R_2$ or $R_3$ bonded to the dioxycarbon through an oxygen linkage, and which polymers are synthesized by reacting a polyol with an orthoester or orthocarbonate. The polymers are useful for making articles of manufacture, including devices and coatings for delivering beneficial agents.

31 Claims, 13 Drawing Figures

DRUG DELIVERY DEVICES MANUFACTURED FROM POLY(ORTHOESTERS) AND POLY(ORTHOCARBONATES)

BACKGROUND OF THE INVENTION

1. Field of the Invention

The present invention relates to polymers. More particularly, the invention pertains to novel and useful polymers comprising a carbon-oxygen backbone having a dioxycarbon moiety with a plurality of organic groups pendant from the dioxycarbon. The polymers are represented by the following general formula:

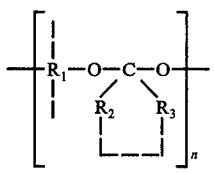

wherein $R_1$ is a di, tri or tetravalent alkylene, alkenylene, alkyleneoxy, cycloalkylene, cycloalkylene substituted with an alkyl, alkoxy or alkenyl, cycloalkenylene, cycloalkenylene substituted with an alkyl, alkoxy or alkenyl, arylene, or a arylene substituted with an alkyl, alkoxy or alkenyl, $R_2$ and $R_3$ are alkyl, alkenyl, alkoxy, alkenyloxy, alkylene, alkenylene, alkyleneoxy, alkenyleneoxy, alkylenedioxy, alkenylenedioxy, aryloxy, aralkyleneoxy, aralkenyleneoxy, aralkylenedioxy, aralkenylenedioxy, oxa, or $OR_1O$ with $R_1$ defined as above; and wherein, (a) $R_1$ is divalent when $R_2$ and $R_3$ are alkyl, alkenyl, alkoxy, or alkenyloxy, with at least one of $R_2$ or $R_3$ an alkoxy or alkenyloxy; (b) $R_1$ is divalent when $R_2$ and $R_3$ are intramolecularly covalently bonded to each other and to the same dioxycarbon atom to form a heterocyclic ring or a heterocyclic ring substituted with an alkyl, alkoxy or alkenyl when $R_2$ is an alkyleneoxy or alkenyleneoxy and $R_3$ is an alkyleneoxy, alkenyleneoxy or alkylene; (c) $R_1$ is divalent when $R_2$ and $R_3$ are intramolecularly covalently bonded to each other and to the same dioxy carbon atom to form a fused polycyclic ring or a fused polycyclic ring substituted with an alkyl, alkoxy or alkenyl when $R_2$ is an oxa, alkyleneoxy or alkenyleneoxy and $R_3$ is aryloxy, aralkyleneoxy, aralkenyleneoxy or aralkylene; (d) $R_1$ is divalent when $R_2$ or $R_3$ is an $OR_1O$ bridge between polymer backbones bonded through their dioxycarbon moieties, and the other $R_2$ or $R_3$ is an alkyl, alkenyl, alkyloxy, or alkenyloxy; (e) $R_1$ is tri or tetravelent when $R_2$ and $R_3$ are covalently bonded to each other and to the same dioxycarbon atom to form a heterocyclic ring or a heterocyclic ring substituted with an alkyl, alkoxy or alkenyl when $R_2$ is an alkyleneoxy or alkenyleneoxy and $R_3$ is an alkyleneoxy, alkenyleneoxy or alkylene; (f) $R_1$ is tri or tetravalent when $R_2$ and $R_3$ are covalently bonded to each other and to the same dioxy carbon atom to form a fused polycyclic ring or fused polycyclic ring substituted with an alkyl, alkoxy or alkenyl when $R_2$ is an oxa, alkyleneoxy or alkenyleneoxy and $R_3$ is aryloxy, aralkyleneoxy, aralkenyleneoxy or aralkylene.

The polymers provided by the invention include homopolymers, copolymers of the random and block types formed by reacting monomers or mixtures of preformed homopolymers and/or copolymers, branched polymers and cross-linked polymers. The invention also makes available to the art thermoplastic linear polymers when $R_1$ is divalent, $R_2$ and $R_3$ are substituted with a noncross-linking group or are bonded intramolecularly; thermosetting cross-linked polymers when $R_1$ is divalent and $R_2$ or $R_3$ is intermolecularly bonded between different polymeric backbones; and, thermosetting cross-linked polymers when $R_1$ is tri or tetravalent and $R_2$ and $R_3$ are substituted with noncross-linking groups, or bonded intramolecularly.

2. Description of the Prior Art

The reaction of orthoesters with glycols leading to non-polymeric and other diverse products is known to the art in the references such as *Ind. J. Appl. Chem.*, Vol. 28, No. 2, pages 53 to 58, 1965 wherein Mehrota, et al obtained monoethoxy-monoglycolate and triglycoxy-bisorthoformate by reacting orthoformate with hexamethylene glycol in molar ratios of one to one, and two to three to yield low molecular weight compounds. Similarly, Crank, et al in *Aust. J. Chem.*, Vol. 17, pages 1392 to 1394, 1964, disclosed the reaction of triols with orthoesters including ethyl orthoformate with butane 1,2,4-triol, pentane-1,2,5-triol and pentane-1,3,5-triol to form monomeric bicyclic compounds. During the preparation of the bicyclic orthoesters by reacting ethyl orthoformate with triols, Crank, et al found that compounds produced from starting materials having a 1,2-diol structure also contained compounds having ethylene linkages. In a subsequent paper, Crank, et al *Aust. J. Chem.*, Vol. 17, pages 1934 to 1938, 1964, developed this reaction into a synthetic procedure for the conversion of 1,2-diols into olefins. Later, DeWolfe in *Carboxylic Ortho Acid Derivatives,* 1970, published by Academic Press, Inc., New York, noted that carboxylic orthoesters are more reactive toward acid hydrolysis than almost any other class of compounds, and this high hydrolytic reactivity complicates their synthesis and storage. DeWolfe reported that the conversion of diols to cyclic orthoesters including alkoxydioxolane or alkoxydioxane, followed by acid hydrolysis, provides a method for monoacylating diols. More recently, Bailey reported in *Polym. Prepr. Amer. Chem. Soc. DIv. Polym. Chem.*, Vol. 13, No. 1, pages 281 to 286, 1972, that the polymerization of spiro orthoesters at ambient and elevated temperatures led to polyesters and polycarbonates of the structures $[-CH_2CH_2CH_2COOCH_2CH_2O-]_n$ and $[-OCH_2OCOOCH_2CH_2CH_2-]_n$.

SUMMARY OF THE INVENTION

The invention concerns a new class of polymers comprising a polymeric backbone having a repeating unit comprising hydrocarbon radicals and a symmetrical dioxycarbon unit with a multiplicity of organic groups bonded thereto. The polymers prepared by the invention have a controlled degree of hydrophobicity with a corresponding controlled degree of erosion in an aqueous or like environment to innocuous products. The polymers can be fabricated by conventional techniques into assorted articles of manufacture having various shapes. The polymers can be used for making devices and coatings for releasing a beneficial agent, as the polymers erode at a controlled rate, and thus can be used as carriers for drugs for releasing drug at a controlled rate to a drug receptor, especially where bioerosion is desired.

DETAILED DESCRIPTION OF THE INVENTION

Figure 1:
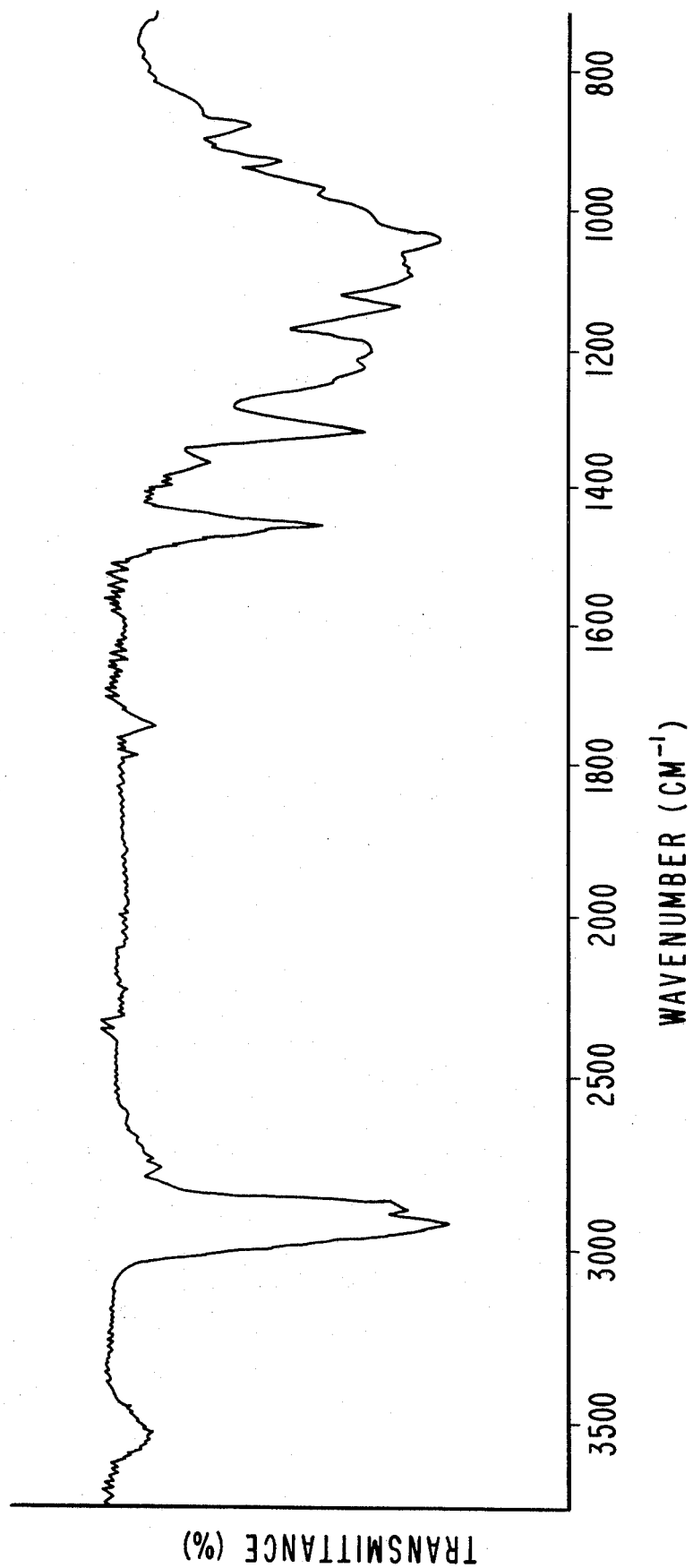

The phrase hydrocarbon radical appearing above and as used elsewhere in the specification, includes, for the purpose of this invention, the terms embraced by $R_1$, $R_2$ and $R_3$ as defined below.

The term alkylene used in this specification for $R_1$ denotes a straight or branched chain divalent, trivalent or tetravalent alkylene radical of 2 to 10 carbon atoms inclusive such as 1,2-ethylene; 1,3-propylene; 1,2-propylene; 1,4-butylene; 1,5-pentylene; 1,6-hexylene; 1,2,5-hexylene; 1,3,6-hexylene; 1,7-heptylene; 2-methyl-1,7-heptylene; 1,8-octylene; 1,10-decylene; 2-propyl-1,6-hexylene; 1,1-dimethyl-1,6-hexylene; and the like. These alkylene chains are derived from the corresponding glycols.

The term alkenylene used for $R_1$ denotes an unsaturated straight or branched chain multivalent radical having 2 to 10 carbon atoms such as 1,4-but-2-enylene; 1,6-hex-3-enylene; 1,7-hept-3-enylene; 1,8-oct-3-enylene; 1,9-non-3-enylene; 4-propyl-(1,6-hex-3-enylene); 5-methoxy-(1,6-hex-3-enylene); 2-propenyl-(1,6-hex-3-enylene); and the like.

The term cycloalkylene as used for $R_1$ includes monocyclic, lower cycloalkylene radicals of 3 to 7 carbons such as cyclopropylene; cyclobutylene; cyclopentylene; cyclohexylene and cycloheptylene. Similarly, the phrase cycloalkylene substituted with an alkyl of 1 to 7 carbons, an alkoxy of 1 to 7 carbons, or an alkenyl of 2 to 7 carbons, includes substituted cycloalkylenes such as 2-methyl-1,3-cyclopropylene; 2-methyl-1,4-cyclopentylene; 2-methyl-1,6-cyclohexylene; 2-ethoxy-2,3-cyclopropylene; 5-butoxy-1,4-cyclopentylene; 2-methoxy-1,4-cyclohexylene; 2-propenyl-1,5-cyclopentylene; 2-isobutenyl-1,6-cyclohexylene; and the like.

Exemplary $R_1$ cycloalkenylene and $R_1$ cycloalkenylene substituted with an alkyl of 1 to 7 carbons, an alkoxy of 1 to 7 carbons, or an alkenyl of 2 to 7 carbons, include monocyclic alkenylenes having from 4 to 7 carbons as ring members, such as 1,4-cyclopent-2-enylene; 1,5-cyclopent-3-enylene; 1,6-cyclohex-2-enylene; 1,6-cyclohex-2-enylene; and the substituted rings such as 5-methyl-(1,4-cyclopent-2-enylene); 6-ethyl-(1,4-cyclohex-2-enylene); 6-ethoxy-(1,5-cyclohex-2-enylene); 2-propyl-(1,5-cyclohex-3-enylene); 2-methoxy-(1,4-cyclohex-2-enylene); 2-methoxy-(1,4-cyclohept-2-enylene), and the like.

The expressions $R_1$ arylene and $R_1$ arylene substituted with an alkyl of 1 to 7 carbons, an alkenyl of 2 to 7 carbons, or an alkoxy of 1 to 7 carbons, include the benzenoid groups such as phenylene, phenylalkylene and phenylalkenylene. Typical groups are 1,4-phenylene; 1,4-phenyldimethylene; 1,4-phenyldiethylene; 2,ethyl-1,4-phenyldimethylene; 2-methyl-1,4-phenyldimethylene; 2-methoxy-(1,4-phenyldimethylene); 2-propyl-(1,4-phenyldiethylene); and the like.

The term alkyl appearing herein for $R_2$ and $R_3$, and as a substituent on the aryl, cycloalkyl and heterocyclic group, embraces straight and branched chain alkyl radicals of 1 to 7 carbon atoms such as methyl; ethyl; n-propyl; n-butyl; n-amyl; n-hexyl; n-heptyl and the various positional isomers thereof such as isopropyl; t-butyl; sec-butyl; isoamyl; isohexyl; t-heptyl and the like.

Exemplary alkenyls as used for $R_2$ and $R_3$, and as a substituent on the aryl, cycloalkyl and heterocyclic group, include the straight and branched chain lower alkenyl groups of 2 to 7 carbons such as 1-propenyl; 2-propenyl or allyl; 1-butenyl; 2-butenyl; 1-pentenyl; 2-ethenyl; and the corresponding positional isomers such as 1-isobutenyl; 2-isobutenyl; 2-sec-butenyl; 2-methyl-1-butenyl; 2-methyl-2-pentenyl; 2,3-dimethyl-3-hexenyl; and the like.

The term alkoxy as used for $R_2$ and $R_3$, and as a substituent on the aryl, cycloalkyl and heterocyclic group, include the straight and branched chain lower alkoxy groups and the positional isomers thereof having 1 to 7 carbon atoms inclusive, for example, methoxy; ethoxy; propoxy; butoxy; n-pentoxy; n-hexoxy; isopropoxy; 2-butoxy; isobutoxy; 3-pentoxy; and the like.

The term alkenyloxy as used for $R_2$ and $R_3$ embraces the straight and branched chain lower alkenyloxy groups and the positional isomers thereof having 2 to 7 carbon atoms, for example, ethenoxy; propenoxy; butenoxy; pentenoxy; hexenoxy; isopropenoxy; isobutenoxy; sec-butenoxy; 2-methyl-1-butenoxy; 2-methyl-2-butenoxy; 2,3-dimethyl-3-butenoxy; and the like.

The term alkyleneoxy appearing in the general formula comprehends, for $R_1$, $R_2$ and $R_3$, straight and branched chain alkyleneoxy radicals of the formula —$OR_4$— wherein $R_4$ is an an alkylene of 2 to 6 carbons, for example, 1,3-propyleneoxy; 1,4-butyleneoxy; 1,5-pentyleneoxy; 1,6-hexyleneoxy; 2,2-dimethyl-1,4-butyleneoxy; and the like. Similarly, the term alkenyleneoxy comprehends, for $R_2$ and $R_3$, radicals of the general formula —$OR_5$— wherein $R_5$ is an alkenylene of 3 to 6 carbons, such as prop-1-enyleneoxy; 1,4-but-1-enyleneoxy; 1,4-but-2-enyleneoxy; 1,5-pent-1-enyleneoxy; 1,6-hex-1-enyleneoxy; and the like.

The expressions alkylenedioxy and alkenyldioxy include the straight and branched chain radicals of the formula —$OR_4O$— wherein $R_4$ is an alkylene of 2 to 6 carbons and of the formula —$OR_5O$— wherein $R_5$ is an alkenylene of 3 to 6 carbons, such as for alkylenedioxy propylenedioxy; butylenedioxy; pentylenedioxy; hexylenedioxy; and heptylenedioxy; and for alkenylenedioxy prop-1-enylenedioxy; 1,4-but-1-enylenedioxy; 1,4-but-2-enylenedioxy; 1,5-pent-1-enylenedioxy; 1,6-hex-1-enylenedioxy; and 1,7-hep-1-enylenedioxy. The phrase heterocyclic ring of 5 to 8 carbons for $R_2$ and $R_3$, defines the ring formed when $R_2$ or $R_3$ is a bond, alkylene or alkenylene, and at least one of $R_2$ or $R_3$ is an alkyleneoxy, alkenyleneoxy, alkylenedioxy or alkenylenedioxy with the terms as defined above.

The terms alkylene and alkenylene used when $R_2$ and $R_3$ are independently taken together to form a ring in cooperation with the carbon of the carbon-oxygen polymeric backbone, include an alkylene of 2 to 6 carbons and an alkenylene of 3 to 6 carbons, such as the alkylenes 1,2-ethylene, 1,3-propylene, 1,4-butylene, 1,5-pentylene, and 1,6-hexylene, and the alkenylenes 1,3-prop-1-enylene, 1,4-but-1-enylene, 1,4-but-2-enylene, 1,5-pent-1-enylene, 1,6-hex-2-enylene, and 1,7-hept-2-enylene.

The terms aryloxy, aralkyleneoxy, aralkenyleneoxy, aralkylenedioxy and aralkenylenedioxy used for $R_2$ and $R_3$ include a radical of 8 to 12 carbons wherein aryloxy is ar—o—, alkyleneoxy is —$OR_4$—, alkenyleneoxy is —$OR_5$—, alkylenedioxy is —$OR_4O$—, alkenylenedioxy is —$OR_5O$—, with $R_4$ an alkylene and $R_5$ an alkenylene as defined above, and ar is phenyl. The phrase fused polycyclic ring of 8 to 12 carbons as used herein, defines a substituent in which a heterocyclic and an aryl ring have two atoms in common, for example, benzfuryl; benzpyranyl; 4,5-benz-1,3-dioxepanyl; 5,6-benz-1,3-dioxepanyl; 4,5-benz-1,3-dioxolanyl; 4,5-benz-1,3-dioxyolanyl; 4,5-benz-1,3-dioxocanyl; 5,6-benz-1,3-dioxocanyl; 6,7-benz-1,3-dioxocanyl; 7,8-benz-1,3-dioxocanyl; and benz-1,3-dioxoanyl.

The term mer as used herein for polymers, copolymers and terpolymers denotes the member unit or the monomeric unit of the polymer. For example, in a homopolymer, the mer units are the same. In a copolymer, the mer unis are different and that can be ordered in the polymer chain in a random fashion when the original units are copolymerized in a common reaction vessel, or they can be ordered in block fashion when the polymers are combined after an initial homopolymerization of each of the different monomeric units. A terpolymer is similar to a copolymer with an added third mer unit.

The novel polymers of the invention are synthesized by intimately contacting and reacting at least one starting polyol with at least one starting compound of the general formula

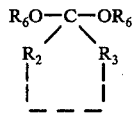

to yield the corresponding polymer.

Exemplary polyols suitable as reactants include diols, triols and the like that can enter into the polymerization reaction without adversely effecting it or the polymeric product. The polyols are known to the art in reported synthesis and they are commercially available. Generally, they include $\alpha,\omega$-aliphatic diols, triols and the like of the straight or branched chain type. Representative polyols are alkane polyols having a terminal hydroxyl group at the terminus of an alkylene chain of the formula

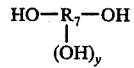

wherein $R_7$ is an alkylene chain of 3 to 12 carbon atoms and y is 0 to 6. Typical diols, named as the glycols include 1,5-pentylene glycols; 1,6-hexylene glycol; 1,7-heptylene glycol; 1,9-nonylene glycol; 2,3-dimethyl-1,6-hexylene glycol; 3,6-diethyl-1,9-nonylene glycol; 1,12-dodecamethylene glycol; and the like.

Polyols containing more than 2 reactive hydroxyl radicals suitable for use herein include polyhydroxyl compounds such as 1,2,3,4,5,6-hexanehexol; 1,2,3-propanetriol; 1,2,5-pentanetriol; 1,3,5-pentanetriol; 1,2,4-butanetriol; 2-methyl-1,2,3-propanetriol; 2-methyl-2(hydroxymethyl)1,2-propanediol; 1,4,7-heptanetriol; 1,5,10-decanetriol; 1,5,12-dodecanetriol; and the like.

Other polyols suitable for synthesizing the polymers include polyglycols containing a repeating glycol monoether moiety —$OCH_2(CH_2)_pOH$ wherein p is 1 to 5, and the polyglycols are diglycols, triglycols, tetraglycols, and the like. Typical polyglycols include diethylene glycol, triethylene glycol, tetraethylene glycol, bis(4-hydroxybutyl) ether, bis(3-hydroxypropyl) ether, and the like.

Additional polyols that can be used in accordance with the invention are polyhydroxyl compounds having 2 or more reactive hydroxyl groups such as pentaerythritol; dipentaerythritol; $\beta$-methylglycerol; 1,4-cyclohexane dicarbinol in the cis, trans isomeric configuration or mixtures thereof; 2,2,4,4-tetramethyl cyclobutane 1,3-diol; adonitol; mannitol; 2,5-dipropyl-1,4-phenyldipropanol; 1,3-cyclopropanol; 2-propenyl-1,4-cyclohexane dipropanol; trimethylol propane; sorbitol; penacol; 2-methyl-1,4-cyclohexane dicarbinol; 3-isopropoxy-1,4-cyclohexane dipropanol; 2-ethenyl-1,3-cyclopentane dicarbinol; 1,4-phenyldicarbinol; 2-propyl-1,4-phenyldiethanol; 3-butoxy-1,4-phenyldibutanol; and the like. The preparation of the above polyols is known to the art in *Acta Pharm. Jugaslav*, Vol. 2 pages 134 to 139, 1952; *Ann.*, Vol. 594, pages 76 to 88, 1955; *J. Am. Chem. Soc.*, Vol. 71, pages 3618 to 3621, 1949; *ibid.*, Vol. 74, pages 2674 to 2675, 1952; *Chem. Abst.*, Vol. 42, pages 8774 to 8775, 1948; *ibid.*, Vol 43, pages 571 to 573 and 6652, 1949; *ibid.*, Vol. 44, pages 2554 and 7231, 1950; *ibid.*, Vol. 46, page 9585, 1952; *ibid.*, Vol. 47, page 7575, 1953; *ibid.*, Vol. 48, page 106, 1954; *ibid.*, Vol. 49, pages 6098 to 6099, 1955; *Encyclopedia of Chemical Technology*, Kirk-Othmer, Vol. 10, pages 638 to 678, 1966, published by Interscience Publishers, New York.

Exemplary starting monomers of the formula

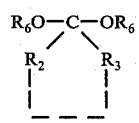

include when $R_2$ and $R_3$ are as previously described and $R_6$ is the same or different straight or branched chain lower alkyl radical of 1 to 7 carbons the esters described below, with the presently preferred alkyl radicals comprising methyl and ethyl. The monomers can be simple or mixed ortho esters. These include trimethylorthoformate, tri-n-butyl orthoformate, tri-hexyl orthoformate, dibutylmonoethyl orthoformate, sec-butyldiethylorthoformate, methyldiethyl orthoformate, ethyldi-isopropyl orthoformate, di-isopropylbutyl formate, and the like. Additional orthoesters include ethylorthoacetate, methylorthoacetate, ethylorthopropionate, methylorthopropionate, sec-butylorthopropionate, propylorthopropionate, and the like ortho esters.

Typical alkenyl orthoester monomers include compounds of the formula $R_2R_3C(OR_6)_2$ wherein $R_3$ is alkenyl as previously described, embracing monomers such as dimethylethenyl orthoformate, diethylpropenyl orthoformate, di-isopropylethenyl orthoformate, dimethylisobutenyl orthoformate, and the like. Also, orthocarbonates including simple or mixed tetraalkyl orthocarbonates such as dipropyl-dimethyl orthocarbonate, diethyl-dimethyl orthocarbonate, tetraethyl orthocrbonate, tetramethyl orthocarbonate, trimethyl-secbutyl orthocarbonate, and the like.

Additional monomers are those of the formula $R_2R_3C(OR_6)_2$ wherein $R_2$, $R_3$ and $R_6$ are alkyl include compounds such as 2,2-dimethoxypropane; 2,2-diethoxypropane; 2,2-dipropoxypropane; 2,2-dimethoxybutane; 2,2-dihexyloxypentane; 2-methyloxy-2-ethoxypropane; and the like. Representative monomers when $R_6$ is alkyl and one of $R_2$ or $R_3$ is alkenyl include the compounds 3,3-dimethyloxy-1-butylene; 3,3-diethyloxy-1-butylene; 3,3-diethoxy-1-hexylene and the like. Also, when $R_2$ and $R_3$ are alkenyloxy, monomers such as 1,2-dimethoxy-1,1-diethenoxyethane; 1,2-diethoxy-1,1-diethenoxyethane; diethenoxyethane; 1,3-diethoxy-2,2-dipropenoxypentane; 1,4-diethoxy-3,3-dibutenoxybutane, and the like.

Monomers embraced by the formula

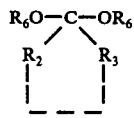

wherein $R_2$, $R_3$ and $R_6$ are as previously defined, and $R_2$ and $R_3$ when taken together form a saturated or unsaturated cyclic or heterocyclic ring includes monomers such as 2,2-dialkoxy-1,3-dioxolane; 2,2-dialkoxy-1,3-dioxanes; 2,2-dialkoxy-1,3-dioxepane; 2,2-dialkoxy-1,3-dioxocane; 2,2-dialkoxy-1,3-dioxonane; 2,2-dialkenyloxy-1,3-dioxolane; 2,2-dialkenyl-1,3-dioxane; 2,2-dialkenyloxy-1,3-dioxepane; 2,2-dialkoxytetrahydrofuran; 2,2-dialkoxypyran; 2,2-dialkoxy-1-ocane; 2,2-dialkoxy-1-oxepane; fused rings such as 2,2-dialkoxy-benz-1,3-dioxolane; 2,2-dialkoxy-benz-1,3-dioxanes; 2,2-dialkoxy-benz-1,3-dioxepane; 2,2-dialkoxy-benz-1,3-dioxocane; 2,2-dialkoxy-benz-1,3-dioxonane; and the like.

Representative of the above monomers substituted with reactive groups include 2,2,5-trimethoxy-3,4-dihydrofuran; 2,2-diethoxy-4,5-benz-1,3-dioxolane; 2,2-dimethoxy-4,5-benz-1,3-dioxolane; 2,2-sec-butyl-4,5-benz-1,3-dioxolane; 2,2-dimethoxyl,3-dioxane, 2,2-diethoxy-1,3-dioxane; 2,2-dipropoxy-1,3-dioxane; 2,2-dimethoxy-4,5-benz-6-keto-1,3-dioxane; 2,2-diethoxy-4,5-benz-6-keto-1,3-dioxane; 2,2-diethoxy-3,4-benz-tetrahydrofuran, 2,2-dimethoxy-4-phenyl-5,6-dihydro-1,3-dioxane; 2,2-dimethoxy-4-phenyl-6-methyl-5,6-dihydro-1,3-dioxane; 2,2-dimethoxy-3,3-dimethyl-5-phenyl-4,5-dihydrofuran; 2,2-diethoxy-3-methyl-5-phenyldihydrofuran; 2,2-dimethoxy-3-propyl-5-phenyl-dihydrofuran; 2,2-dimethoxy-3-phenyl-5,6-benz-3,4-dihydro-1,3-dioxane; 2,2-diethenyloxy-5-methyltetrahydrofuran; 2,2-diethenyloxy-1,3-dioxolane; 2,2-dipropoxy-1-oxapane; 2,2-dibutoxy-1-ocane; 2,2-diethenyloxy-1-oxapane; 2-ethoxy-2-propoxy-1-ocane; 2-isopropoxy-2-ethoxy-1,3-dioxonane; 2,2-diethoxy-5,5-dimethylpyran; 2,2-diethoxy-5-methyl-tetrahydrofuran; and the like.

Other esters of the formula

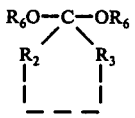

wherein $R_6$ is as defined and $R_2$ and $R_3$ form a cycloalkyl ring include 1,1-dialkoxy cyclopropane; 1,1-dialkoxycyclobutane; 1,1-dialkoxycyclopentane; 1,1-dialkoxycyclohexane; and like monomers such as 1,1-dimethoxycyclobutane; 1,1-diethoxycyclopentane; 1,1-diethoxy-3-dimetholcyclopentane; 1,1-diethoxy-3-proplycyclohexane; and the like.

The above ortho esters and like ortho esters can be prepared according to the following preparations. The Pinner synthesis as described in Ber., Vol. 16, pages 352 to 363, 1883; and ibid., pages 1644 to 1663, 1883, wherein an appropriate nitrite is reacted with an equivalent amount of dry hydrogen halide and an equivalent amount of alcohol to form an iminoester hydrohalide. This is then alcoholized with an excess of alcohol to form the orthoester. The Pinner reaction is set forth as follows: $RCN + R_1OH + HX \rightarrow RC(NH_2X)OR_1 + R_1OH$ $RC(OR_1)_3 + NH_4X$ Orthoesters suitable for the purpose of the invention also can be prepared by the Mkhitaryan reaction as described in Gen. Chem., U.S.S.R., Vol. 8, pages 1361 to 1367, 1938, wherein an alkoxy group of a readily available orthoester such as triethyl orthoacetate or formate are replaced by a higher boiling alcohol or polyol according to the general reaction: $RC(OC_2H_5)_3 + 3R'OH \rightarrow RC(OR')_3 + 3C_2H_5OH$. The orthoesters may also be prepared by alcoholysis of trihaloalkyl groups as set forth in J. Am. Chem. Soc., Vol. 54 pages 2964 to 2966, 1932; as indicated by the following reaction: $RCX_3 + 3NaOR_1 \rightarrow RC(OR_1)_3 + 3NaX$.

The preparation of orthoesters including those of the ring type, is known to the art with ample description of the various methods of preparation as found in U.S. Pat. Nos. 2,409,699; 2,867,667; 3,323,925; and 3,546,188; and in British Pat. Nos. 853,405; and 1,099,559. Also, as found in Synthetic Organic Chemistry, Chapter 16, pages 542 to 545, 1953, published by John Wiley and Sons; in The Chemistry of the Aliphatic Orthoesters, Chapter 2, pages 11 to 43, 1943; Reinhold Publishing Corp.; in Encyclopedia of Chemical Technology, Kirk Othmer, Vol. 8, pages 365 to 383, 1965, Interscience Publishers, New York; Recueil Trav. Chem. Pays, Bes, Vol. 88, pages 897 to 904, 1909; J. Am. Chem. Soc., Vol. 64, pages 1825 to 1927, 1942; Ind. Eng. Chem. Prod. Res. Develop., Vol. 10, No. 4, pages 425 to 428, 1971; J. Am. Chem. Soc., Vol. 71, pages 40 to 46, 1949; Ann. Chem., Vol. 675, page 142, 1964; Angew. Chem., Vol. 69, page 371, 1957; J. Am. Chem. Soc., Vol. 76, pages 5736 to 5739, 1954; ibid., Vol. 77, pages 5601 to 5606, 1955; Chem. Ber., Vol. 89, page 2060, 1956; Aust. J Chem., Vol. 17, pages 1385 to 1398, 1964; Gazz. Chem. Ital., Vol. 96, page 1164, 1966; Chem. Commun., page 13, 1967; and Carboxylic Ortho Acid Derivatives, Chapter 1, pages 1 to 133, 1970, published by Academic Press, New York. The ortho esters can also be prepared by conventional techniques including alcoholysis, condensation, elimination and reduction reactions as described in Organic Functional Group Preparations, by Sandler and Karo, Vol. II, Chapter 2, pages 41 to 68, 1971, published by Academic Press.

The novel polymers of the invention can be synthesized by intimately contacting and reacting a polyol monomer with an orthoester or orthocarbonate monomer to yield the corresponding polymer. Generally, the polymerization reaction is carried out by reacting stoichiometric amounts or an excess of polyol to yield the polymer. That is, the amount of each reactive monomer can be from about 1 to 10 moles of polyol to 1 mole of orthoester or orthocarbonate monomer.

The polymerization of the monomers is carried out in a reaction vessel equipped with a stirrer and vacuum attachment with continuous mixing of the monomers in the presence of a catalyst. The polymerization comprises an initial transesterification reaction followed by a polycondensation reaction with the complete polymerization performed at a temperature of 60° C to 220° C and over a reaction time of 1 hour to 96 hours. The transesterification step of the reaction consists in mixing the monomers and catalyst, and while continuously stirring the monomers, the temperature was gradually raised to 180° C. The transesterification reaction for most monomers, occurs at 75° C to 180° C over a 1 to 12 hour reaction period and at normal atmospheric pressure with continuous distillation of the alcohol. The polycondensation reaction is commenced by reducing the pressure to 0.10 to 0.0001 mm of mercury and, while maintaining the elevated temperature and reduced pressure, carrying out the polycondensation by continuously mixing and reacting the reactants for 12 to 96 hours to yield the polymer.

The polymer is recovered under anhydrous conditions from the reaction vessel by conventional isolation and recovery techniques. For example, the polymer is recovered while hot by extruding or pouring, or the polymer is isolated after cooling, by dissolving it in a dry organic solvent such as benzene, carbon tetrachloride, methylene chloride, dioxane, toluene or xylene, followed by the addition of an organic liquid in which the polymer is insoluble or has limited solubility to precipitate the polymer. Organic liquids for this latter purpose include ether, hexane, pentane, petroleum ether, hexane heptane mixtures, and the like. The polymer is isolated by filtering and drying under anhydrous conditions. Other methods for recovering the polymer include lyophilizing from a solvent.

Representative catalysts for performing the polymerization reaction are Lewis acids such as boron trifluoride, boron trichloride, boron trichloride etherate, boron trifluoride etherate, stannic oxychloride, phosphorous oxychloride, zinc chloride, phosphorous pentachloride, calcium acetate, antimonous oxide mixture, antimony pentachloride, antimony pentafluoride, stannous octoate, stannic chloride, diethyl zinc, n-butyl lithium, and mixtures thereof. The catalysts also include Bronsted catalysts such as p-toluene sulfonic acid, polyphosphoric acid, cross-linked polystyrene sulfonic acid, acidic silica gel, and mixtures thereof. Other catalysts include neutral or basic catalysts such as tetrabutyl titanate, and titanium sodium hydrogen hexabutoxide. The amount of catalyst used is about one part catalyst to about 500 parts of the ester monomer. Smaller or larger amounts can also be used, such as 0.005% to about 2.0% based on the weight of the starting monomer.

The polymerization optionally can be carried out in the presence of an inert organic solvent that does not adversely affect the reaction, or the reaction can proceed in the absence of added solvent. In the latter reaction one of the reactants, for example, the polyol initially serves as the solvent. As polymerization proceeds, solvent by-product is removed from the reaction by conventional distillation, azeotropic distillation, or by distillation under vacuum. Suitable azeotropic solvents include toluene, benzene, m-xylene, cumene, pyridine, and n-heptane.

The following examples are set forth as representative methods illustrative of the spirit of the present invention. These examples are not to be construed so as to limit the scope of the invention as these and other functionally equivalent means will be readily apparent to those skilled in the subject art.

EXAMPLE 1

To 45 grams (0.312 moles) of anhydrous trans-1,4-cyclohexane dicarbinol and 0.05 grams of polyphosphoric acid in a commercially available polymerization reactor was added with constant stirring under an inert nitrogen environment and normal atmospheric pressure 50 grams (0.312 moles) of anhydrous 2,2-diethoxytetrahydrofuran. Next, the mixture was heated to 110°–115° C and held at this temperature for 1½ to 2 hours, with slow distillation of any liquid formed. Then, while maintaining the temperature, the pressure was gradually reduced to 0.01 mm of mercury and at this reduced pressure the temperature was slowly increased to 180° C. The reaction was continued at this temperature for 24 hours. The polymer was isolated by extruding it from the reactor. The polymer had the following structure, where $n$ is the degree of polymerization from 10 to 1000, and the infrared spectrum as seen in FIG. 1.

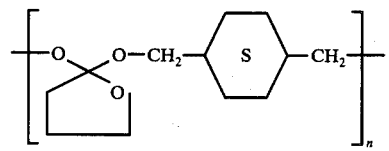

EXAMPLES 2 – 4

Following the procedure of Example 1, but replacing trans-1,4-cyclohexane dicarbinol and 2,2-diethoxytetrahydrofuran with:

trans-2-methyl-1,4-cyclohexane diethanol and 2,2-dimethoxytetrahydrofuran;

trans-2-methyl-1,4-cyclohexane dipropanol and 2,2-dimethoxytetrahydrofuran; and, trans-2-ethyl-1,4-cyclohexane dicarbinol and 2,2-diethoxy-5-methyl-3,4-dihydrofuran; the following polymers are formed:

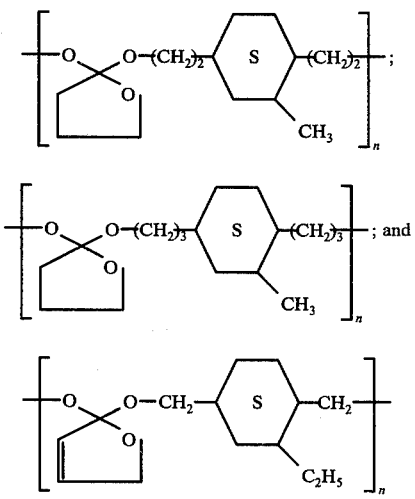

EXAMPLE 5

Repeating the procedure of Example 1, but replacing 2,2-diethoxytetrahydrofuran with a 2,2-di-alkoxytetrahydrofuran selected from the group of 2,2-dimethoxytetrahydrofuran; 2,2-dipropoxytetrahydrofuran; 2,2-dibutoxytetrahydrofuran; the corresponding polymer of the following formula is obtained.

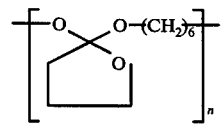

EXAMPLE 6

To 45 grams (0.312 mole) of dry cis-trans-1,4-cyclohexane dicarbinol and 0.05 grams of p-toluene sulfonic acid was added with constant agitation, 50.5 grams (0.312 mole) of 2,2-dimethoxy-5-methyl-1,3-dioxolane and the polymerization reaction of Example 1 repeated to yield the polymer shown below.

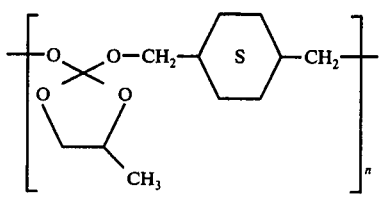

EXAMPLE 7

Figure 2:
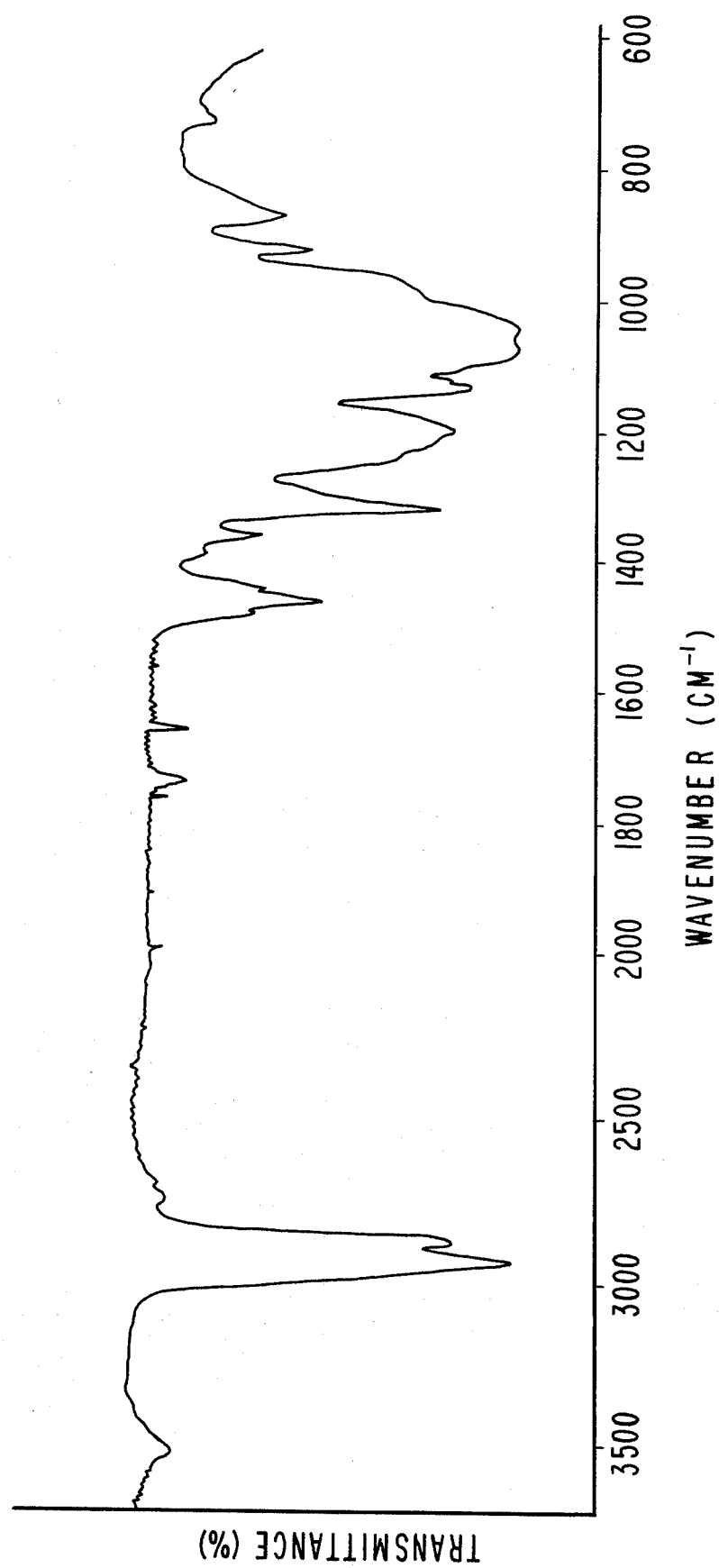
Figure 3:
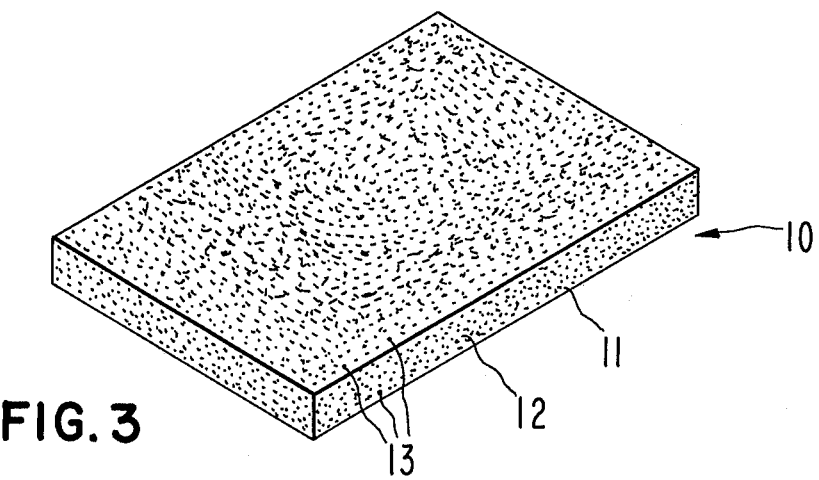
Figure 4:
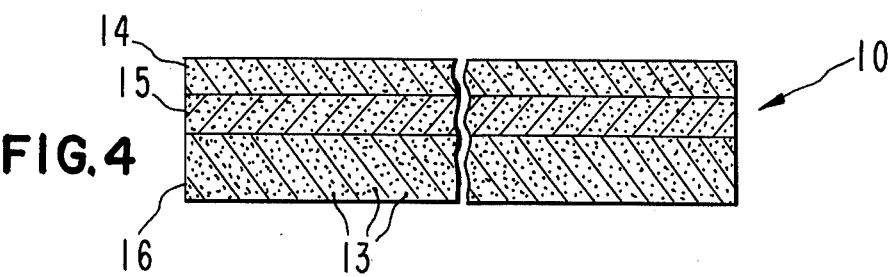

To a mixture of 44.2 grams (0.375 mole) of freshly distilled 1,6-hexanediol and 0.05 gram of polyphosphoric acid under a nitrogen blanket at atmospheric pressure was added with constant stirring 60.0 grams (0.375 mole) of 2,2-diethoxytetrahydrofuran and the mixture heated to 110° to 115° C. The mixture was held at this temperature for 1.5 to 2 hours as ethanol slowly distilled from the reactor. Then, the pressure was reduced to 0.01 mm Hg over a 2 hour period and at this vacuum the temperature was elevated to 180° C over a similar 2 hour period. The reaction was allowed to continue for 24 hours to yield the polymer with the structure shown below ($n$ is 10 to 1000). The infrared spectrum for the polymer is seen in accompanying FIG. 2.

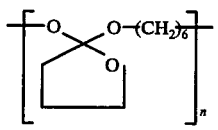

EXAMPLE 8

To 54.7 grams (0.312 mole) of 1,10-decane diol and 0.05 grams of polyphosphoric acid in a reactor vessel under a nitrogen environment and at atmospheric pressure was added with constant stirring 50.0 grams (0.312 mole) of 2,2-diethoxytetrahydrofuran. Next, the mixture was heated to 110° to 115° C and held at this temperature for 1.5 to 2 hours as ethanol gently distilled from the reactor. Then, while maintaining this temperature, the pressure was reduced to 0.01 mm of mercury and at this reduced pressure the temperature was raised to 180° C. The polycondensation was continued for 24 hours to yield the polymer with the structure shown below and with a degree of polymerization of 10 to 1000.

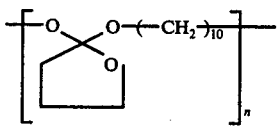

EXAMPLE 9

Repeating the procedure of Example 8, but replacing 1,10-decane diol and 2,2-diethoxytetrahydrofuran with stoichiometric amounts of the monomers 1,4,7-heptanetriol and 2,2-diethoxy-1,3-dioxolane, the following polymer is obtained.

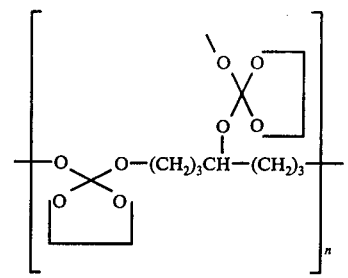

EXAMPLE 10

To 7.38 grams (0.625 mole) of 1,6-hexane diol and 0.10 grams of polyphosphoric acid was added 100.0 grams (0.625 mole) of 2,2-diethoxytetrahydrofuran and 81.0 gram (0.562 mole) of trans-cyclohexane dicarbinol, and the polymerization carried out according to the procedure of Example 1. The random copolymer obtained had a molecular weight, ($\overline{Mw}$) of 11,500 and the following structure, wherein $n$ is 10 to 1000.

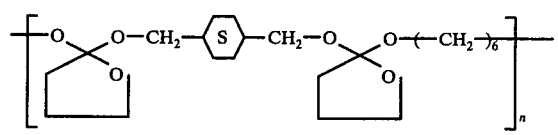

EXAMPLE 11

The procedure of Example 1 and 7 was repeated in this example, and all conditions and reagents were as described except that in this example, the reactive diol was 1,7-heptane diol instead of 1,6-hexane diol. The random copolymer recovered had the indicated structure, wherein $n$ is 10 to 1000.

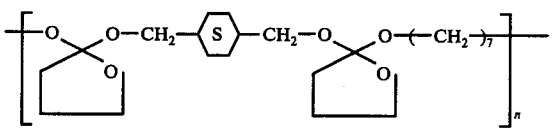

EXAMPLE 12

1.71 grams (2.85 mmole) of glycolaldehyde and 4.66 grams (2.90 mmole) of 2,2-diethoxytetrahydrofuran were mixed and continuously stirred under an inert gas at 120° C and normal atmospheric pressure for 30 minutes to insure mixing of the reactive monomers. Next, trace amounts of Lewis acid catalyst was added and the pressure gradually decreased to 60 mm Hg. The ethanol was distilled into a side-arm borosilicate flask. Then, the pressure was reduced to 0.1 mm Hg and the reaction continued for 3 hours. Finally, the temperature was raised to 180° C, the pressure reduced to 0.06 mm Hg and the polycondensation continued for 20 hours. The polymer formed is soluble in tetrahydrofuran and has the following structure:

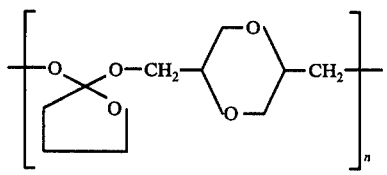

EXAMPLE 13

To 66.3 grams (0.625 moles) of diethylene glycol and 0.1 gram of polyphosphoric acid in a stainless steel polymerization reactor was added 100 gram (0.625 moles) of 2,2-diethoxytetrahydrofuran with constant stirring under an argon backflow, and the reactants heated to 110°–115° C for 2 hours with distillation of ethanol formed during the transesterification step. Then, while holding the temperature constant, the pressure was reduced from atmospheric to 0.01 mm Hg and held there with the temperature slowly elevated to 180° C. The polycondensation was allowed to proceed for 24 hours under these conditions to yield the polymer shown below.

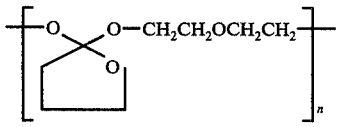

EXAMPLES 14 – 18

The procedure of Example 13 was followed in these examples, with all the reaction conditions as described, except the monomers of the previous example were replaced with stoichiometrically equivalent amounts of the following monomers:

(a) 1,5-pentylene glycol and 2,2-dipropoxy-4-methyltetrahydrofuran;

(b) 2,3-dimethyl-1,6-hexylene glycol and 2,2-dipropoxy-5-methyltetrahydrofuran;

(c) 3,6-dimethyl-1,9-nonylene glycol and 2,2-dipropoxy-5-ethyl tetrahydrofuran;

(d) 1,6-hexylene glycol and 2,2-diethoxy-3,4-dihydrofuran; and (e) 1,6-hexylene glycol and 2,2-diethoxy-5-methyl-3,4-dihydrofuran; to yield the following polymers:

a) 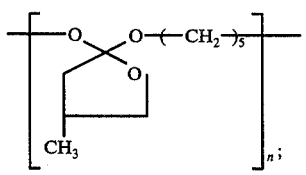

b) 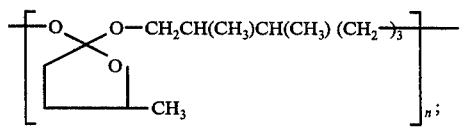

c) 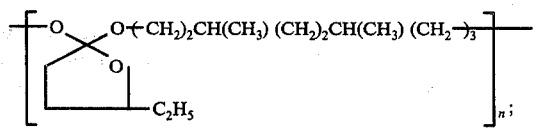

d) 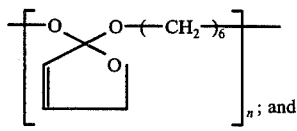

e) 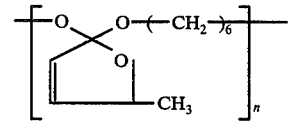

EXAMPLES 19 – 21

The procedure employed in Example 13 was followed in these examples with all the reaction conditions as previously described. The starting monomers listed below were used in equivalent amounts for those of Example 13. The monomers are:

2,2,4,4-tetramethylcyclobutane 1,3-diol and 2,2-diethoxytetrahydrofuran;

triethylene glycol and 2,2-diethoxy-5,5-dimethyltetrahydrofuran;

triethylene glycol and 2,2-diethoxy-5-methoxytetrahydrofuran; to yield the following polymers, wherein $y$ is 3 and $n$ is 10 to 1000.

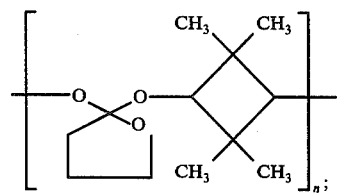

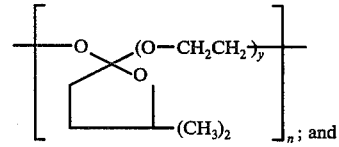

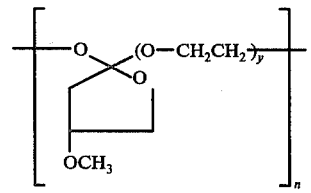

EXAMPLE 22

To a mixture of polyol monomers consisting of 41.58 grams (0.284 mole) of trans-cyclohexane dicarbinol; 7.53 grams (0.071 mole) of the oxyalkylene glycol; diethylene glycol and 0.057 gram of polyphosphoric acid was added 56.7 gram (0.355 mole) of diethoxytetrahydrofuran under the inert gas argon and the mixture heated to 115° C for 2 hours with continuous distillation of the liquid organic by-product. Then, while keeping the temperature constant, the pressure was reduced to 0.01 mm of Hg and at this reduced pressure the temperature was raised to 180° C. The reaction was continued at this temperature and vacuum for 24 hours. The random copolymer was isolated by extruding it from the reactor and it had the following configuration where $n$ is 10 to 1000.

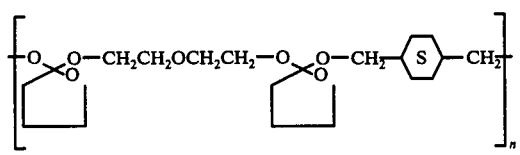

EXAMPLE 23

The procedure used for preparing the copolymer in Example 22, was repeated in this polymerization; all conditions were as described. The monomers used in this example were 2,2-diethoxytetrahydrofuran, 1,6-hexanediol and a mixture of cis-trans-1,4-cyclohexane dicarbinol. The structure of the copolymer obtained is as follows:

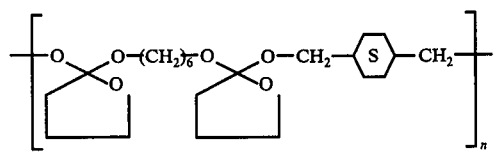

EXAMPLE 24

To 2.3 grams (0.0195 mole) of 1,6-hexanediol was added with stirring 12.5 grams (0.078 mole) of 2,2-diethoxytetrahydrofuran and the mixture heated to 150° C for 3 hours under nitrogen to form an end-capped diol which was collected at 146°–154° C, and 0.1 mm Hg. The end-capped diol has the following structure:

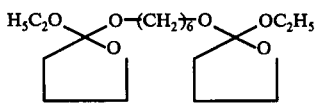

Next, 3 grams (0.00087 moles) of the freshly prepared end-capped diol was heated with an additional 1 equivalent of 1,6-hexanediol in a polymerization flask under nitrogen at 100°–120° C for one hour, with condensation first removed by simple distillation and then by distillation under reduced pressure (0.2 mm Hg) at 120° C, to yield a polymer of the following structure:

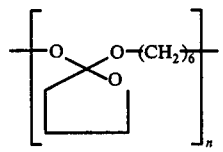

EXAMPLE 25

To 14.77 grams (0.125 mole) of 1,6-hexanediol was added 20.0 g (0.125 mole) of 2,2-diethoxytetrahydrofuran and 20 mg of p-toluene sulfonic acid and the monomers reacted according to the procedure of Example 1 to yield poly(2,2-dioxohexamethylene tetrahydrofuran) having a molecular weight of 15,700. Separately, 45 grams (0.312 moles) of cis-trans-1,4-cyclohexane dicarbinol and 0.05 grams of p-toluene sulfonic acid was added to 50 grams (0.312 moles) of 2,2-diethoxytetrahydrofuran and the monomer reacted according to the procedure of Example 1 to yield poly-(2,2-dioxo-cis,-trans-cyclohexanedimethylene tetrahydrofuran) having a molecular weight of 24,700. Then, 9.5 grams (0.051 mole) of the poly(2,2-dioxohexymethylene tetrahydrofuran) was copolymerized with 10.76 grams (0.051 mole) of poly(2,2-dioxo-cis,trans-cyclohexanedimethylene tetrahydrofuran) for 43 hours at 180° C under 0.01 mm Hg in the presence of trace amounts of acid catalyst to yield the block copolymer of the following formula, when the ratio of $m$ to $n$ is 1 to 1, and the degree of polymerization is 10 to 1000:

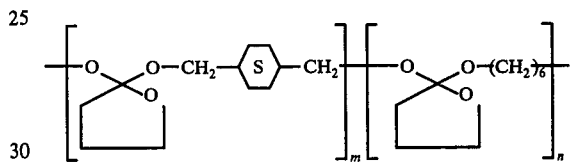

EXAMPLE 26

13.26 grams (0.125 mole) of diethylene glycol was added to 20.0 grams (0.125 mole) of 2,2-diethoxytetrahydrofuran, and the monomers reacted in the presence of a Lewis acid catalyst for 42 hours according to the general procedure in Examples 11 and 12 to yield a polymer having a molecular weight of about 20,000. Separately, 50.0 grams (0.312 mole) of trans-1,4-cyclohexane dicarbinol and 50 grams (0.312 mole) of 2,2-diethoxytetrahydrofuran were reacted according to the procedure of Example 1 to yield another polymer. Next, 5.94 grams (0.0341 mole) of the former polymer was mixed with 14.5 grams (0.0682 mole) of the latter polymer and the reaction carried out at 180° C, and under 0.01 mm Hg for four days to yield a block copolymer. The copolymer was dissolved in benzene and lyophilized for later use. The structure of the copolymer is as follows:

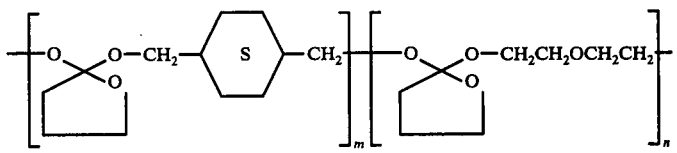

EXAMPLES 27 – 30

The procedure of Example 1 was followed in this example, with all the reaction conditions identical to those as previously set forth; however, the monomer of Example 1 was replaced with the monomers set forth below:

(a) 2,2-dimethoxy-4,5-benz-1,3-dioxolane (61.5 gram, 0.3 mole) and 1,6-hexamethylene diol (39.5 grams, 0.3 mole);

(b) 2,2-dimethoxy-4,5-benz-1,3-dioxoane (66.3 grams, 0.3 mole) and 3-hexenylene-1,6-diol (48.3 grams, 0.3 mole);

(c) 2,2-diethoxy-4,5-benz-1,3-dioxolane (106 grams, 0.5 mole) and diethylene glycol (41 grams, 0.5mole); and, (d) 2,2-diethoxy-1,methylcyclohexyl ortho carbonate (73 grams, 0.3 mole) and 1,6-hexamethylene diol (39.3 grams, 0.3 mole); to yield the following polymers:

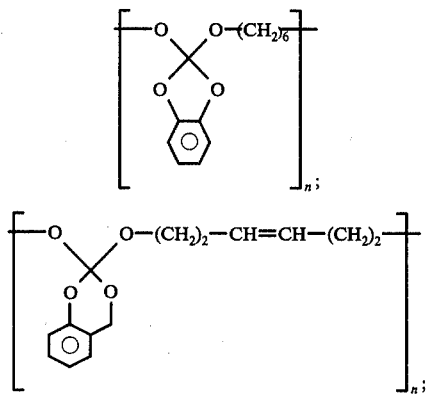

a)

b)

c)

d)

EXAMPLE 31

136 grams (1.0 mole) of anhydrous 1,3,3,5-pentane tetraol and 0.075 grams of titanium sodium hydrogen hexabutoxide are added to 162 grams (1.0 mole) of anhydrous 2,2-diethoxy-1,3-dioxolane and the reactants stirred to produce a homogenous mixture. Next, the mixture is heated to 115° C for 2 hours with distillation of the continuous forming liquid into a side-arm collector. Then, with the temperature constant, the pressure is reduced to 0.01 mm Hg and at this pressure the temperature is raised to 180° C, with the reaction continued at the raised temperature for 48 hours to yield the polymer below.

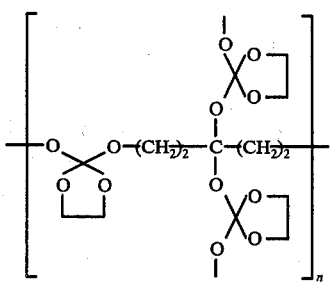

EXAMPLES 32 – 35

Following the procedure of Example 31, with all reaction conditions as described, except that the polyols and heterocyclic ortho ester of the example are replaced with the following monomeric pairs:

(a) 1,3,5-pentane triol, 120 grams, and asymetrical 2-propoxy-2-ethoxy5-methyl-1,3-dioxolane, 178 grams;

(b) 1,10-decanediol, 174 grams, and 2,2-diethoxy-5-methyl-1,3-dioxane, 180 grams;

(c) 1,10-decanediol, 174 grams, and 2,2-diethoxy-1,3-dioxepane, 178 grams; and, (d) 1,6-hexanediol, 122 grams, and 2,2-diethoxy-1,3-dioxocane, 218 grams; to yield the following polymers:

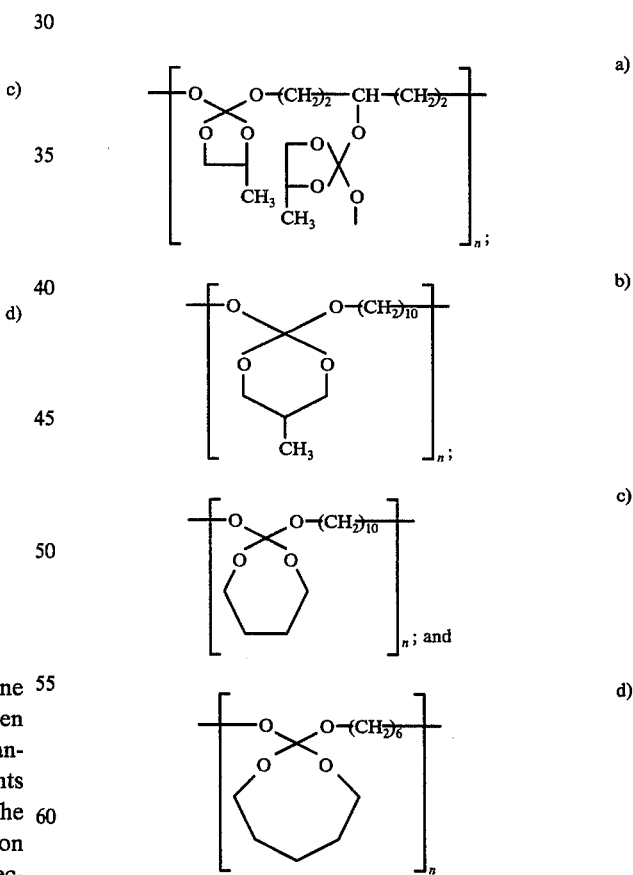

a)

b)

c)

d)

EXAMPLES 36 – 39

Repeating the procedure of Example 31, the transesterification and polycondensation steps are repeated with the following reactive monomers:

(a) 1,6-hexanediol, 122 grams, and 2,2-diethoxytetrahydropyran, 174 grams;
(b) 1,6-hexanediol, 122 grams, and 2,2-diethoxy-5,5-dimethyl-tetrahydropyran, 202 grams;
(c) 1,6-hexanediol, 122 grams, and 2,2-diethoxy-1-oxepane, 188 grams; and,
(d) 1,6-hexanediol, 122 grams, and 2,2-diethoxy-Δ³-oxyepin, 172 grams; to yield the following polymers where $n$ is 10 to 1000:

a) 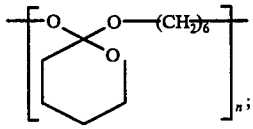

b) 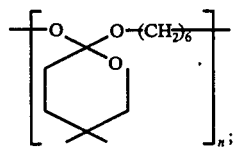

c) 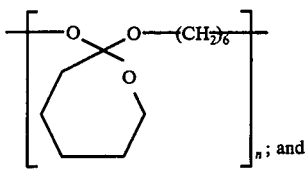; and d) 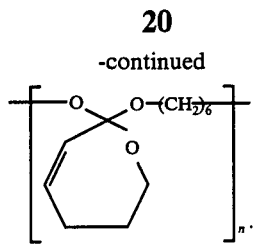

EXAMPLES 40 – 44

In Table 1 below, copolymers prepared according to the spirit of the invention are structurally illustrated. In the table, "No." refers to the polymer; "Ratio" is the ratio of "$m$" and "$n$"; "Type" is "B" for block copolymer and "R" is for random copolymer and the degree of polymerization is 10 to 1000.

Table 1

| No. | Ratio | Type | Polymer |
|---|---|---|---|
| 40 | 1:1 | B | |
| 41 | 1:2 | B | |
| 42 | 4:1 | R | |
| 43 | 4:1 | R | |
| 44 | 4:1 | R | |

EXAMPLE 45

In the present example, polymers having the general formula set forth below are prepared, wherein $R_1$ is as previously defined, $b$ is 2 to 6, and $n$ is to 10 to 1000:

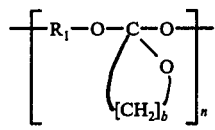

To 50 grams (0.312 mole) of diethoxytetrahydrofuran was added 45 grams (0.312 mole) of trans-cyclohexanedicarbinol and 0.05 grams of polyphosphoric acid and the monomers introduced into a polymerization reactor under a positive nitrogen flow to form a reaction mixture. Next, the mixture was stirred at 60 rpm at 110°–115° C and at atmospheric pressure for 1.5 hours with slow distillation of ethanol. Then, the pressure was reduced to 0.01 mm Hg over a 2 hour period. When the high vacuum was attained, the temperature was increased to 180° C over a period of about 2 hours, and the polymerization was terminated after 24 hours of reaction time with the polymer extruded from the reactor into a Teflon ® coated beaker. The polymer had a $\overline{M}n$, number average molecular weight of $1.63 \times 10^4$, a $\overline{M}w$ weight, average molecular weight of $7.70 \times 10^4$, a DP, degree of polymerization, of 77 and a $\overline{M}w/\overline{M}n$ equal to 4.69. The polymer has the following structure:

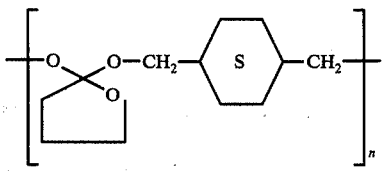

EXAMPLES 46 – 48

In Table 2, polymers prepared according to Example 45 from the monomers 2,2-diethoxytetrahydropyran, 2,2-diethoxy-1-oxepane, 2,2-diethoxy-oxecane and trans-cyclohexane dicarbinol are illustrated.

following monomers were used: 2,2-diethoxytetrahydrofuran, 50 grams (0.312 mole) and 1,10 decanediol, 54.7 grams (0.312 mole) with 0.05 grams of polyphosphoric catalyst. The polymerization reaction is as follows:

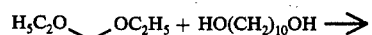 

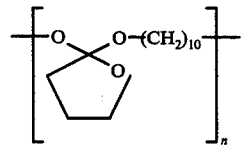

wherein the polymer had a $\overline{M}w = 5.78 \times 10^4$, $\overline{M}n = 5.98 \times 10^3$, and a $\overline{M}w/\overline{M}n = 9.66$.

EXAMPLE 50

The procedure of Example 45 was repeated in this example with all conditions as described except for the following: 2,2-diethoxytetrahydrofuran 100.0 grams (0.625 mole); trans-cyclohexane dicarbinol 81.0 grams (0.562 mole); 1,6 hexanediol 7.38 grams (0.0625 mole); and polyphosphoric acid 0.10 grams; with a polymerization time of 18.5 hours. The random polymer produced had the following properties as measured by gel permeation chromatography calibrated with polystyrene standard: $\overline{M}w = 11,500$, $\overline{M}n = 3,600$; $\overline{M}w/\overline{M}n = 3.2$. The synthesis and polymer is as follows:

Table 2

| No. | Monomer | Monomer | Polymer |
|---|---|---|---|
| 46 | {H₅C₂O, OC₂H₅ 6-ring with O} | HOH₂C—⟨S⟩—CH₂OH | [—O—⟨O⟩—O—CH₂—⟨S⟩—CH₂—]ₙ |
| 47 | {H₅C₂O, OC₂H₅ 7-ring with O} | HOH₂C—⟨S⟩—CH₂OH | [—O—⟨O⟩—O—CH₂—⟨S⟩—CH₂—]ₙ |
| 48 | {H₅C₂O, OC₂H₅ 8-ring with O} | HOH₂C—⟨S⟩—CH₂OH | [—O—⟨O⟩—O—CH₂—⟨S⟩—CH₂—]ₙ |

EXAMPLE 49

The procedure of Example 45 was repeated in this example with all conditions as described except the

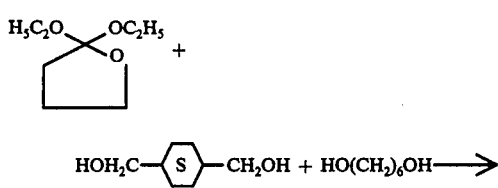

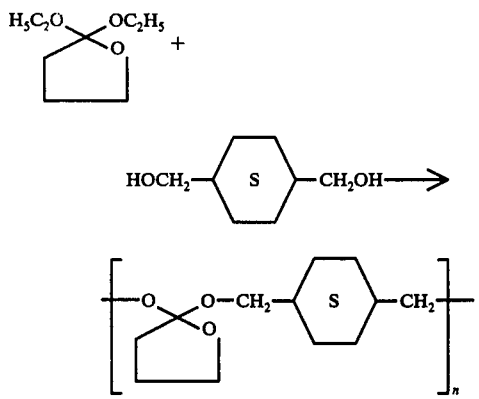

EXAMPLE 51

The procedure of Example 50 was followed in this example and all conditions were as previously described except, the monomers were 2,2-diethoxytetrahydrofuran 100 grams (0.625 mole) and 1,6-hexanediol 73.7 grams (0.625 mole). The yield was 89 g, and the polymer had a $\overline{Mw} = 18\times10^3$, $\overline{Mn} = 3.5\times10^3$, and $\overline{Mw}/\overline{Mn} = 5.4$.

EXAMPLE 52

A mixture consisting of 140 grams (0.874 mole) of 2,2-diethoxytetrahydrofuran, 124.7 grams (0.865 mole) of trans-cyclohexane dicarbinol and 0.14 grams of polyphosphoric acid was heated to 130° C for 5 hours in an $N_2$ atmosphere for transesterifying the monomers. Then, with the temperature at 130° C, the pressure was reduced to 0.01 mm Hg over a 2 hour period, followed by the temperature being increased to 180° C, with the distillation of a viscous material, having a vapor temperature of 150° C. During the exothermic stage, heat was applied only to the bottom of the flask. The exothermic stage subsided after 4 hours and the heat was then applied to the whole flask. After 96 hours of reaction time, at 180° C, the polymerization was terminated. The work-up procedure consisted of dissolving the polymer in 400 ml of dry benzene, followed by filtration and lyophilization. The yield was 159 g, with $\overline{Mn} = 9,000$, $\overline{Mw} = 34,000$, and $\overline{Mw}/\overline{Mn} = 3.7$. The polycondensation reaction is as follows:

EXAMPLE 53

50 grams of 2,2-diethoxytetrahydrofuran and 28.1 grams of 1,4-butane diol previously mixed with 0.05 grams of polyphosphoric acid, were reacted for 3.25 hours over an increasing temperature span of 70° to 130° C, and under atmospheric pressure according to Example 45. Then the reactants were heated under reduced pressure of 120 mm to 2.4 mm Hg for 4 hours at 110° to 125° C to yield 1,6,8-trioxa-spiro(4,6)undecane. The spiro compound was polymerized in a sealed tube at 125° C in the presence of a Lewis acid catalyst, i.e. $SbF_5$, $PF_5$ or $BF_3$, to yield the polymer, where $n$ is 10 to 1000.

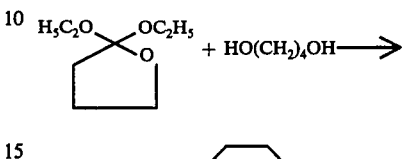

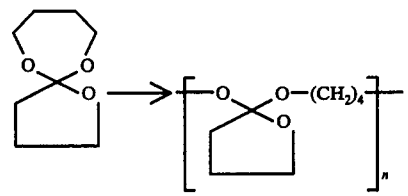

EXAMPLE 54

The polycondensation of 2,2-diethoxytetrahydrofuran and 30/70 cis/trans-cyclohexanedimethanol with polyphosphoric acid was carried out as follows: the catalysts' weight ratio to diethoxytetrahydrofuran was 1/500, the monomer ratio of cyclohexanedicarbinol to tetrahydrofuran was 2.2/1, and the cyclohexanedicarbinol was introduced into the reactor as a 68% weight solution in methanol. The methanol was distilled from the diol in situ, and toluene was added to azeotrope water from the system. The tetrahydrofuran was then added and transesterification and polycondensation carried out at 180° C and at a vacuum of 24 millitors over a 24 hour period. The recovered yield was 82%. GPC analysis was as follows: $\overline{Mw} = 36,000$, $\overline{Mn} = 8,500$, $\overline{Mw}/\overline{Mn} = 4.3$. The polymer prepared by the example was embraced by the following formula:

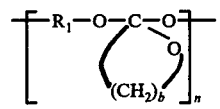

wherein $b$ is 2 to 6 and $n$ is 10 to 1000, and it had the specific formula as follows:

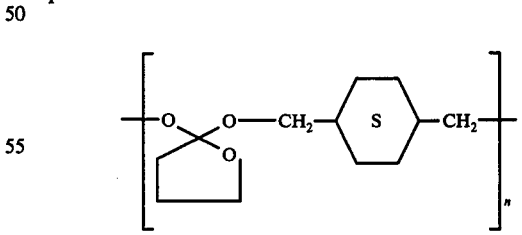

EXAMPLE 55

The polycondensation of 2,2-diethoxytetrahydrofuran and 30/70 cis, trans-2-methyl-1,6-cyclohexanedimethanol with the acid catalyst polyphosphoric acid was carried out using a catalyst weight ratio to tetrahydrofuran of 1/500, and a monomer ratio of lower alkyl substituted cyclohexanedicarbinol to the monomeric cyclic orthoester of 2.2/1 as follows: first the cyclohexanedicarbinol was introduced into the reactor as a 68% weight solution in anhydrous methanol, with the methanol distilled from the diol in situ, followed by the addition of toluene and the catalyst to azeotrope water from the reaction system. Next, tetrahydrofuran was added and polycondensation carried out at 180° and under a vacuum of 24 millitors over a 24 hour period to yield the polymer having a molecular weight in excess of 35,000. The polymer prepared is represented by the general formula:

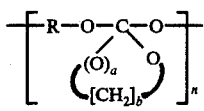

wherein $n$ is 0 or 1, $b$ is 2 to 6 and $n$ is greater than 10, generally 10 to 1000 or higher. The polymer yield was 80% and it had the following structure:

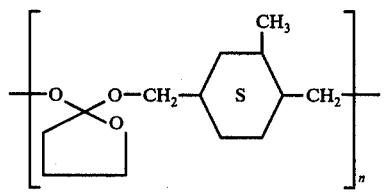

EXAMPLES 56 – 58

The procedure set forth in Example 55 is repeated in these examples, with all reaction conditions as previously described, except the following monomers are substituted for those previously set forth:

2,2-diethoxytetrahydrofuran and 5-methyl-1,6-cyclohex-$\Delta^2$-enedicarbinol;

2,2-dipropoxy-1,3-dioxolane and 2-ethenyl-1,6-cyclohexanedipropanol; and 2,2-diethoxy-5-methyl-1,3-dioxolane and 3-methyl-1,5-cyclopentanediethanol, to yield the following polymers:

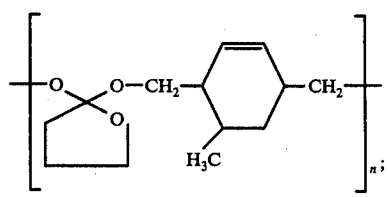

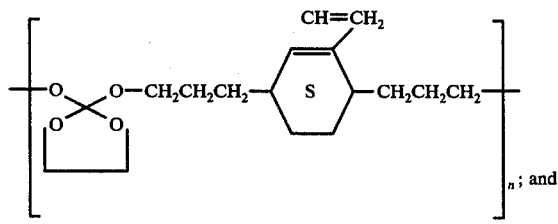

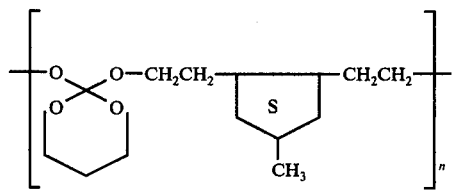

EXAMPLES 59 – 66

In the instant examples, polymers are provided according to the procedure of Example 55. The polymers are prepared by reacting a cyclic ortho carbonate monomer with a polyol wherein the monomer pairs are as follows:

2,2-dialkoxy-1,3-dioxolane and 1,6-hexamethylene diol;

2,2-dialkoxy-1,3-dioxolane and 1,4-phenylene dicarbinol;

2,2-dialkoxy-1,3-dioxane and 1,7-heptamethylene diol;

2,2-dialkoxy-1,3-dioxepane and 2-methyl-cis-trans-1,6-cyclohexanedipropanol;

2,2-dialkoxy-1,3-dioxocane and 3-ethyl-1,5-cyclopentane diethanol;

2,2-dialkoxy-1,3-dioxonane and 1,6-cyclohex-2-enediethanol;

2,2-dialkoxy-1,3-dioxolane and 3-hexenylene-1,6-diol; and 2,2-dialkoxy-1,3-dioxolane and 1,6-cyclohexane dibut-2-enyl diol; to yield the corresponding polymers of the formula:

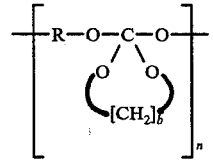

wherein $b$ is 2 to 6, $n$ is 10 to 1000 and the polymers are as follows:
poly(2,2-dioxohexamethylene-1,3-dioxolane);
poly(2,2-dioxo-1,4-phenyldimethylene-1,3-dioxolane);
poly(2,2-dioxo-2-methyl-cis,trans-1,6-cyclohexanedipropylene-1,3-dioxepane);
poly(2,2-dioxo-3-ethyl-1,5-cyclopentane diethylene-1,3-dioxocane);
poly(2,2-dioxo-1,6-cyclohex-2-ene diethylene-1,3-dioxonane),
poly(2,2-dioxo-1,6-hex-3-enelene-1,3-dioxolane);
poly(2,2-dioxo-1,6-cyclohexane dibut-2-eneylene-1,3-dioxolane).

EXAMPLE 67

The polycondensation of 2,2-diethoxytetrahydrofuran with 1,6-hexanediol in the presence of p-toluene sulfonic acid catalyst with the catalyst having a weight ratio of 1/500 to the 2,2-diethoxytetrahydrofuran and the monomer ratio of 2.2/1 of hexanediol to diethoxytetrahydrofuran was carried out as follows: first, the hexanediol was introduced into the reactor and mixed with freshly distilled toluene. Then, toluene was distilled in situ to azeotrope water from the system. Next, the diethoxytetrahydrofuran and p-toluene sulfonic acid were added and transesterification and polycondensation carried out at 180° C and 10 millitors of vacuum over a 27 hour period to yield the polymer, having a GPC analysis as follows: $\overline{Mw} = 92{,}000$; $\overline{Mn} = 10{,}000$; $\overline{Mw}/\overline{Mn} = 9.2$.

EXAMPLES 68 – 69

Repeating the procedures of Examples 54 and 55, copolymers and terpolymers are synthesized from polyols, orthoesters, orthocarbonates and preformed polymers to yield polymers having the following generic formula:

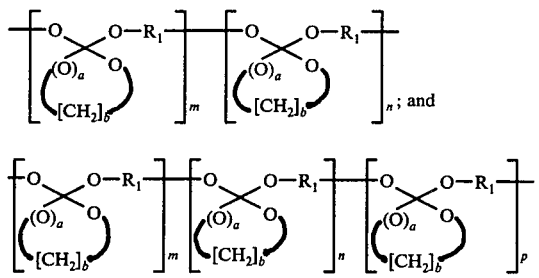

wherein $a$ is 0 or 1; $b$ is 2 to 6; $R_1$ is independently the same or different in each repeating polymeric unit, where $R^1$ is as defined previously, and $n$, $m$, and $p$ are 10 to 1000.

EXAMPLE 70

13.26 grams (0.125 mole) of diethylene glycol was added to 20.0 grams (0.125 mole) of 2,2-diethoxytetrahydrofuran and the monomers reacted in the presence of a Lewis acid for 42 hours according to Examples 11 and 12 to yield poly(2,2-dioxodethylene glycol tetrahydrofuran). Separately, 50.0 grams (0.312 mole) of trans-1,4-cyclohexane dicarbinol and 50.0 grams (0.312 mole) of 2,2-diethoxytetrahydrofuran was reacted according to Example 1 to yield poly(2,2-dioxo-transcyclohexane dimethylene tetrahydrofuran). Separately, 14.77 grams (0.125 mole) of 1,6-hexanediol was added to 20.0 grams (0.125 mole) of 2,2-diethoxytetrahydrofuran and 20 mg of p-toluene sulfonic acid, and the monomers reacted according to Example 1, to yield poly(2,2-dioxohexamethylene tetrahydrofuran). Then, 0.51 mole of poly(2,2-dioxodiethylene glycol tetrahydrofuran), 0.51 mole of poly(2,2-dioxo-trans-cyclohexane dimethylene tetrahydrofuran) and 0.51 mole of poly(2,2-dioxohexamethylene tetrahydrofuran) was polymerized for 50 hours at 180° C under 0.01 mm Hg in the presence of trace amounts of acid catalyst to yield the terpolymer.

Example 1 to yield 46.2 grams of polymer. The polymer had a $\overline{Mn}$ of 10,000, an $\overline{Mw}$ of 36,000, an $\overline{Mw}/\overline{Mn}$ of 3.6 and a structural formula as follows:

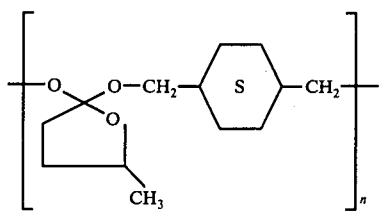

DETAILED DESCRIPTION OF APPLICATION OF THE INVENTION

The polymers of the invention are useful for making articles of manufacture including devices and coatings for releasing beneficial agents. The polymers can be processed into articles, including delivery devices and coated onto an agent by standard manufacturing techniques. For example, the polymers can be extruded into filaments, spun into fibers, pressed into shaped articles, solvent film cast, doctor-bladed into thin films, coated onto an agent by solvent evaporation, coated by using a fluidized bed, compression and transfer molded, and processed by like standard methods of manufacture.

The polymers of the invention can be used as a single film, in a number of layers made of the same or of different polymers, and they can be made into devices of various geometric shapes, for example flat, square, round, tubular, disc, ring, and the like. Also, the devices of the invention are sized, shaped and adapted for implantation, insertion or placement on the body, in body cavities and passageways, or for positioning in other environments of use for example, streams, aquariums, fields or reservoirs. Standard procedures for processing polymers are described in *Plastic Encyclopedia*, Vol. 46, pages 62 to 70, 1969.

The polymers of the invention are useful for making devices for dispensing an active agent, as they have a controlled degree of hydrophobicity in the environment of use and because they erode into innocuous products at a continuous rate which exhibits no known deleterious effects on the environment or towards an animal body.

The term "hydrophobicity" as used above and in the remainder of the specification broadly refers to the property of the polymers not to absorb appreciable amounts of water. For the purpose of the subject invention, the hydrophobic polymers when they do absorb water, do not absorb it in an amount exceeding 5 per-

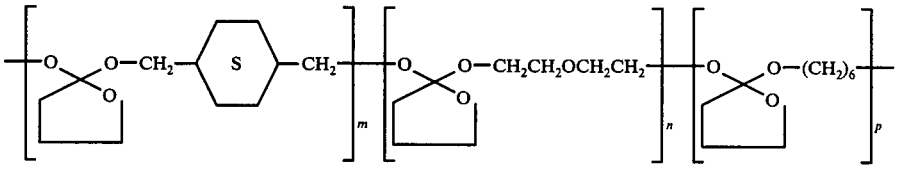

EXAMPLE 71

68.2 grams of trans-cyclohexane dicarbinol and 0.1 grams of polyphosphoric acid were added to 50 grams of 5-methyl-2,2-diethoxytetrahydrofuran, that was previously treated with sodium to remove any traces of ethanol and the polymer polymerized according to cent of their dry weight.

The terms "erodible" and "bioerodible" as used herein define the property of the polymers to break down as a unit structure or entity in a non-biological or in a biological environment over a period of time to innocuous products. The terms "erosion", "bioerode" and "bioerosion" generally define the method and environment where breakdown or degradation of the polymer occurs.

The phrase "prolonged period of time" as used herein, generally means the period between the start of erosion or the breakdown of the polymers when the polymers are placed in a moisture laden environment and that period in time when the polymer is gone. Depending upon the structure and dimensions of the device, such as number of layers and thickness, the period may continue over days, several months such as ninety days, one hundred and eighty days, a year or longer. The environment includes aqueous and aqueous-like biological environments.

The polymers are, as previously noted, useful for making devices for releasing a wide variety of active agents. The term "agent" as used in the specification and accompanying claims includes any compound, mixture of compounds, composition of matter consisting of a compound and a carrier, which when released from a device produces a beneficial and useful result. The term "active agent" includes pesticides, herbicides, germicides, biocides, algicides, rodenticides, fungicides, insecticides, plant growth promoters, plant growth inhibitors, preservatives, disinfectants, sterilization agents, cosmetics, drugs, plant foods, vitamins, sex sterilants, plant hormones, fertility inhibitors, fertility promoters, air purifiers, micro-organism attenuators, and nutrients.

The term "drug" as comprehended by active agent, broadly includes physiologically or pharmacologically active substances for producing a localized or systemic effect or effects in mammals including humans and primates, avians, valuable domestic household, sport or farm animals such as sheep, goats, cattle, horses, etc., or for administering to laboratory animals such as mice, rats and guinea pigs. That is, the device of the invention can be used for administering drugs that are active at a point in near relation to the delivery device, or, for administering drugs which will produce a response at a site remote from the point of application of the drug delivery device. The drugs that may be administered include inorganic and organic drugs without limitation, are those drugs that can be transported across a vessel, for example, drugs acting on the central nervous system such as hypnotics and sedatives, mixtures thereof such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and α-bromo-isovaleryl urea; and hypnotic and sedative urethanes and disulfanes; narcotic antagonists such as naloxone and cyclazocine; psychic energizers such as isocarboxazid, nialamide, phenelzine, imipramine, tranylcypromine and paraglyene; tranquilizers such as chloropromazine, promazine, fluphenazine, reserpine, deserpidine; meprobamate and benzodiazepines such as chlordiazepoxide; anticonvulsants such as primidone, diphenylhydantoin, ethltoin, phenetruide and ethosuximide; muscle relaxants and antiparkinson agents such as mephenesin, methocarbomal, trihexylphenidyl, biperiden and levo-dopa, also known as L-dopa and L-β-3-4-dihydroxyphenylalanine; analgesics such as morphine, codeine, meperidine and nalorphine; antipyretics and anti-inflammatory agents such as aspirin, salicylamide and sodium salicylamide; local anesthestics such as procaine, lidocaine, naepaine, piperocaine, tetracaine, and dibucane; antispasmodics and antiulcer agents such as atropine, scopolamine, methscopolamine, oxyphenonium, papaverine and prostaglandins such as $PGE_1$, $PGE_2$, $PGF_{1\alpha}$, $PGF_{2\alpha}$, and PGA; anti-microbials such as penicillin, tetracycline, oxytetracycline, chlorotetracycline, and chloramphenicol; sulfonamides; anti-malarials such as 4-aminoquinolines, 8-aminoquinolines and pyrimethamine; antivirals including idoxuridine, hormonal agents such as prednisolone, cortisone, cortisol and triamcinolone; androgenic steroids, for example methyltestosterone and fluoxmesterone; estrogenic steroids, for example, 17β-estradiol and ethinyl estradiol; progestational steroids, for example, 17α-hydroxyprogesterone acetate, 19-nor-progesterone, norethindrone and progesterone; sympathomimetic drugs such as epinephrine, amphetamine, ephedrine, and norpinephrine; cardiovascular drugs, for example, procainamide, amyl nitrite, nitroglycerin, dipyridamole, sodium nitrate, and mannitol nitrate; diuretics, for example, chlorothiazide, and flumethiazide; antiparasitic agents such as bephenium hydroxynaphthoate, dichlorophen, dapsone and enitabas; neoplastic agents such as mechlorethamine, uracil mustard, 5-fluorouracil, 6-thioquaniine, and procarbazine; hypoglycemic drugs such as insulin, isophane insulin suspension, protamine zinc insulin suspension, globin zinc insulin, extended insulin zinc suspension, and other like insulins derived from animal and synthetic origin including tolbutamide, acetohexamide, tolazamide, and chloropropamide; nutritional agents, for example vitamins such as ascorbic acid, essential amino acids, essential elements such as iron, and essential fats; ophthalmic drugs such as pilocarpine base, pilocarpine hydrochloride, pilocarpine nitrate, eserine salicylate, atropine sulfate, homatropine, and eucatropine. The above drugs are further described in *The Pharmacological Basis of Therapeutics*, Edited by Goodman and Gilman, 4th Edition, 1970, published by The Macmillan Company.

The agents or drugs also can be in various forms, such as uncharged molecules, components of molecular complexes, pharmacologically acceptable salts such as hydrochloride, hydrobromide, sulfate, laurates, palmatates phosphate, nitrate, borate, acetate, maleate, tartrate, oleates, and salicylates. For acidic drugs, salts of metals, amines, or organic cations, for example quaternary ammonium can be employed. Furthermore, simple derivatives of drug such as esters, ethers, and amides which have solubility characteristics that are suitable for the purpose of the invention. Also, an agent or drug that is water insoluble can be used in a form that is a water soluble derivative thereof to effectively serve as a solute, and on its release from the device, it is converted by enzymes, hydrolyzed by body pH, or metabolic processes to the original form or to a biologically active form. Additionally, agent or drug formulation within the devices can have various art known forms such as solution, dispersion, paste, cream, particle, granule, emulsions, suspensions and powders.

Representative of other active agents suitable for use with the devices of this invention include without limitation, insecticides applied to immature insects, namely during the embryo, larvae or pupae stage as effecting metamorphosis and leading to abnormal development, death or the inability to reproduce. These include aliphatic α β-unsaturated esters having a lower alkoxy groups which are effective for Hemipteran such as Lygaeidae, Miridae and Pyrrhocoridae; Lepidropteran such as Pyralidae, Noctuidae and Gelechiidae; Coleopteran such as Tenebrionidae, Crysomelidae and Dermestidae; the Dipteran mosquitos and flies; Homopteran such as asphids and other insects. The compounds are delivered at dosage levels of the order of 0.01 micrograms to 25.0 micrograms per insect.

Figure 5:
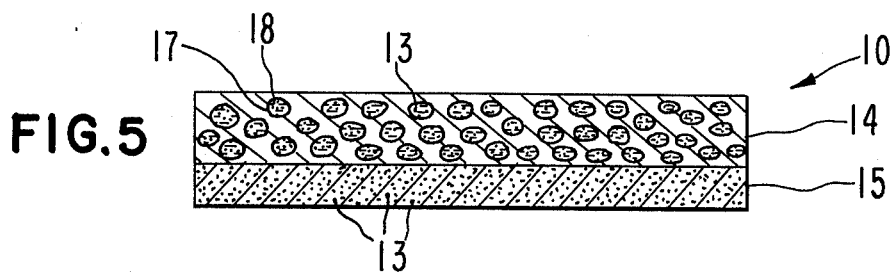

Additional representative agents include cyclopentane insecticides of the formula:

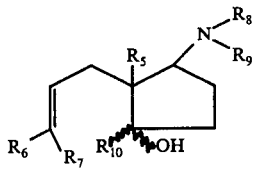

wherein $R_6$, $R_7$, $R_{10}$, $R_8$ and $R_9$ are selected from the group consisting of lower alkyl and $R_5$ is a member selected from the group consisting of methyl and ethyl, for use against Lepidoptera, Diptera and Coleoptera. The device can also be used to deliver juvenile hormones such as methyl-10,11-(cis)osido-7-ethyl-3,11-dimethyltrideca-2(trans), 6(trans)-dienoate and methyl-10,11(cis)oxido-3,7,11-trimethyltrideca-2(trans), 6(trans)-dienoate. Other agents which can be delivered include 2,3,5-trichloropyridine-4-ol; 4-(methylthio)-3,5-xylyl N-methyl carbamate; O-isopropoxyphenyl N-methyl carbamate; O,O-dimethyl S(N-methylcarbamoyl) methyl phosphorodithioate; and 2,4-dichlorophenoxyacetic acid.

The polymers prepared according to the invention, are useful for coating numerous agents such as for providing slow release fertilizers. The fertilizers are coated in their conventional form such as granules, powder and beads. Fertilizers that can be coated include the urea, fertilizers with slow ammonia release, fertilizers in the form of salts such as elements of carbon, nitrogen, phosphorus, sulfur, potassium, calcium, magnesium, manganese, zinc, copper and boron and the like. Additionally, the fertilizer can be impregnated into, or suitably admixed with inert materials such as silica and coke.

The polymers, in view of the stated properties, are especially useful as bioerodible, agent-release, rate controlling materials as they bioerode at a controlled and continuous rate concurrently with the release of agent at a corresponding controlled and continuous rate. Devices made with the present polymers are reliable and easy to use for releasing an agent as they normally require intervention or handling only at the time when the device is positioned in the environment of use or the animal. Additionally, the devices can be made to release an agent at a zero order rate or at a variable rate by controlling the molecular weight and composition of the polymer, by controlling the concentration of the agent in the polymer and the surface area exposed, and by making the devices with different polymers that undergo bioerosion and agent release at different rates. Examples of devices made available to the art by the invention are described below the devices in the figures and specification are for administering an active agent, mainly a drug, and these devices are set forth to illustrate various embodiments of the invention. That is, they are not to be construed as limiting as other devices will be apparent to those versed in the art from the specification, the drawings and the accompanying claims. Also, the devices in the drawings are not necessarily drawn to scale and like parts in related figures are identified by like numbers.

In FIG. 3, a device 10 prepared by using a polymer of the invention, is seen comprising a wall 11 forming a matrix made of bioerodible polymer 12 having an agent 13, a drug in this embodiment, dispersed therein. Device 10 can be used for the continuous administration of a locally active drug to an organ, mucosa, derma, or to any local drug receptor, or device 10 can be used for administering a systemically active drug for transport from the place of administration by the circulatory system to produce a physiologic or pharmacologic response at a distant site. In one embodiment, device 10 is square shaped having dimensions of 3 in. × 3 in. × 10 mil, and it was made by mixing into poly(2,2-dioxo-trans-1,4-cyclohexane dimethylene tetrahydrofuran) hydrocortisone as follows: 2.375 grams of the polymer was heated in a laboratory, Teflon® flat coated pan equipped with a surface thermometer to about 150° C, and then 0.125 grams of micronized hydrocortisone was added to the polymer. Next, the polymer and hydrocortisone were thoroughly mixed to produce a good dispersion of the drug, and to yield a 5% hydrocortisone loaded polymer. After the pan cooled to room temperature, the polymer drug formulation was removed from the pan and solid film prepared by pressing the polymer at 250° F (121.1° C), and at 10,000 psi for 5 minutes with a 10 mil, 3 in. × 3 in. spacer, positioned between Teflon® sheets. The devices were prepared under an essentially dry, inert atmosphere using oven dried apparatus. Device 10 surface bioerodes in an aqueous environment at a controlled and continuous rate of about two microns of depth per hour. Concurrently, hydrocortisone is released at a like controlled and continuous, but proportional rate. Device 10 can be used for the management of inflammation, and bursitis when applied to a drug receptor site.

In FIG. 4, a device 10 is seen for administering an agent 13 at variable rates over a period of time. Device 10 is a multilayered structure comprised of two outer layers 14 and 16, distant from each other with a layer 15 positioned between layers 14 and 16. All the layers can be made of different bioerodible polymers, or layers 14 and 16 can be made of the same polymer with layer 15 made of a different polymer. An agent 13 is dispersed in each layer and it can be the same or different in the layers. In operation, when outer layer 14 has bioeroded at a controlled and continuous rate to release agent 13, middle layer 15 is exposed and releases its agent at a rate corresponding to the bioerosion rate of the polymer. When layer 15 has bioeroded away, layer 16 is exposed and begins to bioerode and release its agent over a period of time. Many variations of device 10 of FIG. 4 will be apparent to those skilled in the art of dispensing, especially drug delivery. For example, a greater number of layers can be used, a variety of agents including drugs, can be used in the several layers, and polymers having different bioerosion rates can be used for obtaining different delivery patterns.

In one embodiment, device 10 of FIG. 4 is designed for releasing a drug and it is made by using as its outer layers 14 and 16, the polymer drug formulation used in FIG. 3, with layer 15 made of a different polymer drug formulation. Layer 15 has the same dimensions as layers 14 and 16 and it is made by mixing into 2.375 grams of poly(2,2dioxotrans-1,4-cyclohexane dimethylene-5-tetrahydrofuran) 0.125 grams of micronized hydrocortisone and processing the polymer drug mixture as described in FIG. 3. Then, the three layers are pressed together to give the device of FIG. 4.

FIG. 5 illustrates another device 10 made by using the bioerodible polymers of the invention. Device 10 is a means for delivering an agent 13 including a drug, that is difficult to disperse within the subject polymers. Device 10 consists of two layers 14 and 15, each formed of a different polymer having a different bioerosion rate. Layer 14 consists of a polymeric matrix containing a plurality of cells 17 dispersed throughout the matrix. An agent 13 is present in cells 17, which agent is dissolved in a liquid 18 that is a solvent for the agent and a nonsolvent for the polymer. Layer 15 can have the same thickness or a different thickness as layer 14, and it contains particles of a different agent 13 dispersed therein. When device 10 is placed in the environment of use, for example against an animal organ, or in a body cavity, layer 14 gradually bioerodes and releases dissolved agent 13 to the surrounding tissues. After layer 14 has disappeared, bioerosion proceeds to layer 15 with layer 15 bioeroding and releasing dispersed agent 13 to surrounding tissue. Many variations of device 10 will be apparent to those skilled in the art. For example, a greater number of layers can be used, a variety of agents, including drug, dosage forms can be employed in the layers, and different polymers having different bioerosion rates can be used in different layers. Device 10 can be made by known prior art techniques which form closed cells and entrap liquids. One such technique suitable for the present purpose is the solvent precipitation technique. This technique consists in using at least two miscible liquids with at least one of the liquids a non-solvent for the polymer and having a lower volatility than the other liquids. In preparing a device, first the polymer and the liquids are mixed to form a single phase. Next, the liquids, which have higher volatilities than the non-solvent, are removed by evaporation to form a film containing a plurality of discrete closed cells having entrapped therein droplets of non-solvent, which is the liquid in the cells. The liquid serves as a carrier for beneficial agents, for example medicines, deodorants, fungicides and disinfectants.

Figure 6:
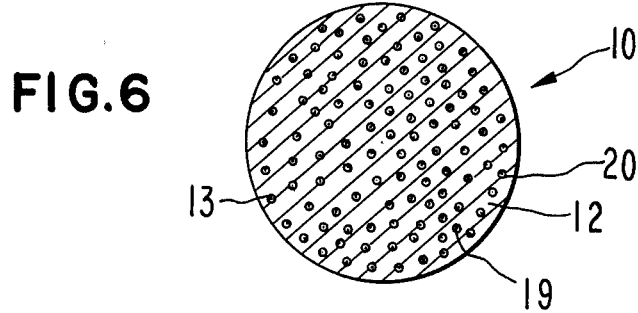

FIG. 6 illustrates a device 10 formed of a bioerodible polymer 12 comprising a multiplicity of microcapsules 19 with each microcapsule having a wall 20 made of an agent release rate controlling material. An agent 13 is housed within microcapsules 19. Device 10 can be manufactured with different designs, for example in one embodiment, microcapsules 19 are present in polymer 12 in clusters, while in another embodiment, microcapsules 19 are uniformly distributed throughout polymer 12. Device 10, when placed in the environment of use, bioerodes at a controlled and continuous rate releasing microcapsules 19 to the surrounding tissues which then dispense agent 13 by passage through release rate controlling wall 20. The microcapsules used herein can be made by standard coacervation methods. The coacervation method consists essentially of the formation of three immiscible phases, a liquid manufacturing phase, a core phase and a coating phase with deposition of the liquid polymer coating on the core material and rigidizing the coating, usually by thermal, cross-linking or desolvation techniques to form microcapsules. The microcapsules made by the above technique have an average size of from several tenths of a micron to 5,000 microns, although this feature is not critical to the practice of the invention. Techniques for preparing microcapsules, such as the classic Bungenberg de Jong and Kass method are reported in *Biochem. Z.*, Vol. 232, pages 338 to 345, 1931; *Colloid Science*, Vol. 11, "Reversible System", edited by H. R. Kruyt, 1949, Elsevier Publishing Company, Inc., New York; *J. Pharm. Sci.*, Vol. 59, No. 10, pages 1367 to 1376, 1970; *Remington's Pharmaceutical Science*, Vol. XIV, pages 1676 to 1677, 1970, Mack Publishing Company, Easton, Pennsylvania; and in German Pat. No. 1,939,066.

Figure 7:
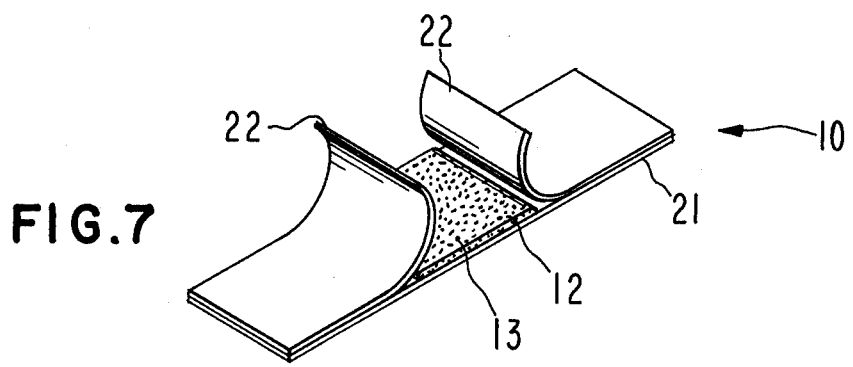

In FIG. 7, a device of aid in the healing of injuries is shown comprising a support base layer 21 formed of a breathable impervious material such as cellophane, rubber or polyethylene and the like, with a bioerodible solid polymer 12 containing agent 13, a drug, fixed to base 21. A protective facing material 22, such as coated paper, plastic film or crinoline is adapted to overlay polymer 12, and it is removed prior to application of device 10. Device 10 is useful for administering drug 13 to the skin, mucosa or an exposed wound simply by applying the device for the controlled release of drug as polymer 12 bioerodes. After the therapeutic program is completed, device 10 is removed and discarded.

In another embodiment, not shown, device 10 is an ointment consisting of a polymer 12 and a drug 13 and it was prepared as follows: to 2.375 grams of the viscous polymer poly(2,2-dioxo-1,6-hexamethylene tetrahydrofuran), having a molecular weight of about 25,000, was added 0.125 grams of $11\beta,17,21$-trihydroxypregn-4-ene-3,20-dione and the ingredients thoroughly mixed for 5 minutes to yield device 10. The mixing was done with standard laboratory blending equipment, at room temperature, and in a dry, inert atmosphere. Device 10 is useful for the controlled and continuous release of drug 13 when applied to the environment of use by inunction.

Figure 8:
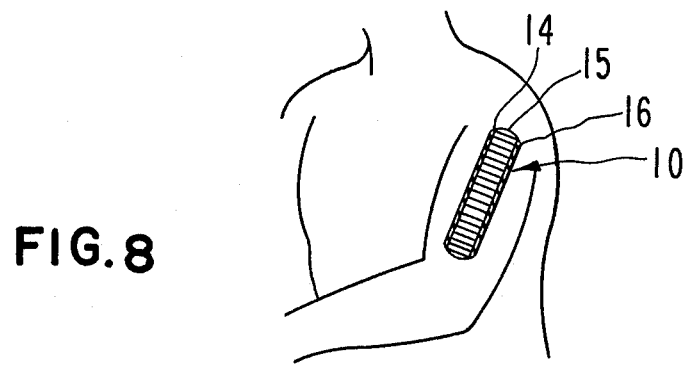

FIG. 8 depicts a pharmaceutical device particularly adapted for use as a depot implant. Depot implant 10 is manufactured for administering a drug 13 and it is comprised of a pair of layers 14 and 16 having sandwiched therebetween a single layer 15. Layers 14 and 16 are made from the same or different biodegradable polymers and they have the same or different drug incorporated therein. Layer 15 is made from a different polymer having a different bioerosion rate than layers 14 and 16, while optionally, it can contain the same or a different drug. Drug delivery is accomplished by placing implant within the animal body, thereby administering drug at a controlled and continuous rate over a prolonged period of time. One advantageous use of the implant is in surgical operations accompanied by severe pain after the operation is completed and the patient regains consciousness. In these cases, when the body is opened for the operation, an implant containing an analgesic can be implanted into the body during the operation to ease pain as it bioerodes and releases the analgesic drug throughout the recovery period.

In addition to the surgical implants 10 as just described, the invention also provides injectable implants made of the novel polymers 12 of the invention. These implants are useful for releasing drugs 13 over a prolonged period of time at various rates for example 200, 600 or 1200 $\mu$g per day. An injectable implant comprising a polymer having an erosion rate of about 2 microns per hour in a biological aqueous environment with a physiological pH of 6 to 8 and a drug concentration of 5% was prepared as follows: To 2.375 g of poly(2,2-dioxo-trans-1,4-cyclohexane dimethylene tetrahydrofuran) was added 0.125 g of hydrocortisone and the ingredients heated to 150° C to give a melt. The drug was dispersed throughout the melt by mixing the ingredients for 5 minutes to give a good dispersion. The mixing was performed in a dry, inert environment, at atmospheric pressure, and with dry equipment. Next, after the polymer cooled to room temperature, it was transferred to a press and injection molded into a solid, cylindrical shaped implant, 3 mm in diameter by 8 mm long. The implant was positioned in a muscle of an animal by trochar injection where it bioeroded and released steroid for the management of inflammation.

A similar implant containing 20% progesterone in poly(2,2-dioxo-trans-1,4-cyclohexane dimethylene tetrahydrofuran) having an original weight of about 114 mg, had an in vivo release rate of progesterone, expressed in mg per day over a 7 day period, as follows: 3.7; 3.2; 2.9; 2.2; 2.5; and 3.8 mg respectively.

Another injectable implant containing norethisterone was prepared by dispensing the drug in poly(2,2-dioxo-trans-1,4-cyclohexane dimethylene tetrahydrofuran) according to the procedure set forth above, except that drug and polymer were blended at 130° C in a dry helium atmosphere. The implant formed had a drug concentration of 20% and a cylindrical shape. The implant was placed bilaterally in the paravertebral muscles of rabbits by trochar injection where it bioeroded at a controlled and continuous rate concomitantly with the release of norethisterone at a rate of 600 µg per day.

Figure 9:
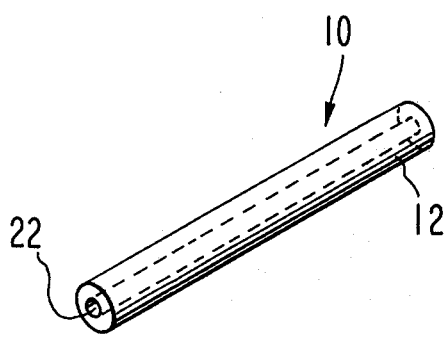
Figure 10:
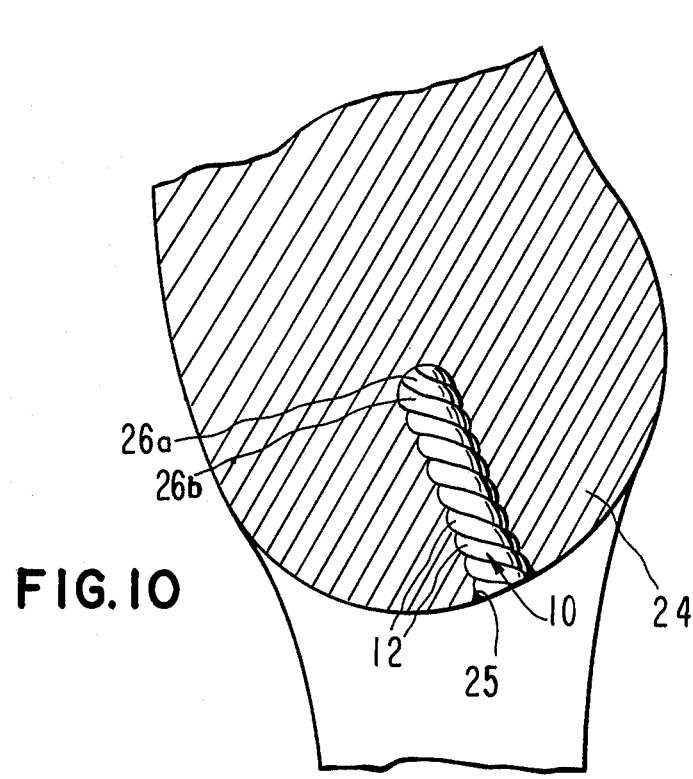

FIGS. 9 and 10 illustrate devices for delivering drug, which devices have several variables that may be manipulated to control the rate and period of drug release. Referring first to FIG. 9, there is illustrated a device 10 having a cylindrical shape and a passageway 20 extended through the center of device 10 in parallel alignment to the cylindrical axis of device 10. Device 10 is made of a bioerodible polymer 12 for releasing drug within a vagina. Passageway 20 is a means for manipulating the amount of drug released from device 10 by increasing the surface exposed to the fluid of the environment of use thereby influencing the amount of drug released over bioerodible time. FIG. 10 illustrates another means for manipulating the rate and period of drug release from a device 10, and it provides the medical profession with a device for insertion into the natural cavities of the animal body 24, such as the anus 25, where it releases a drug for promoting healing effects. Device 10, as seen in FIG. 10, is made of two fibers 26a and 26b, with one fiber 26a intertwisted with fiber 26b to provide a dual element device 10. Fibers 26a and 26b are made of the like or unlike bioerodible polymers 12 containing the same or different drugs, thereby providing means for influencing drug release throughout the drug release period by varying the polymer and the drug.

Figure 11A:
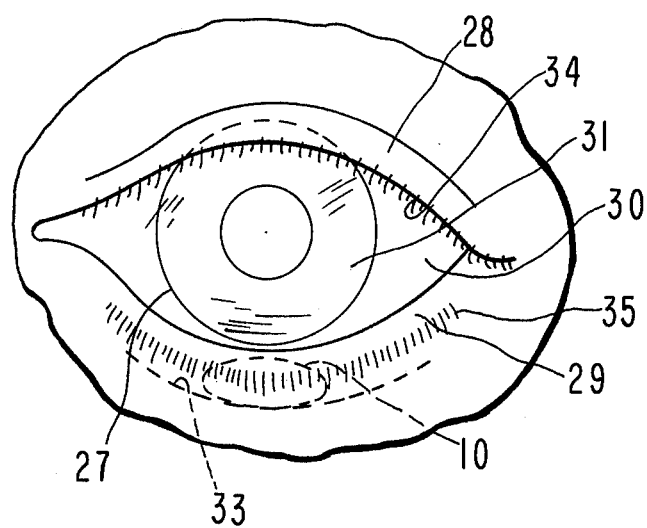
Figure 11B:
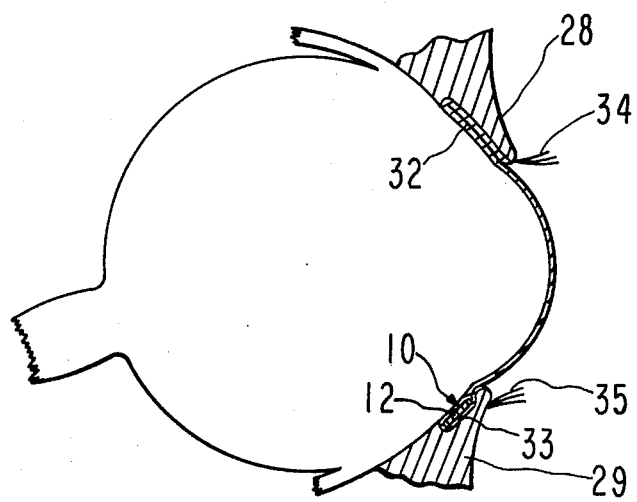

Referring to FIGS. 11a and 11b, a device 10 is shown for placement in a human eye comprising an eyeball 27 having an upper eyelid 28 and a lower eyelid 29, respectively, with the eyeball 27 covered for the greater part of its area by the sclera 30 and at its central portion, by the cornea 31. The eyelids 28 and 29 are lined with an epithelial membrane or palpebral conjunctiva. The sclera 30 is lined with the bulbar conjunctiva which covers the exposed portion of eyeball 27. The cornea 31 is covered with an epithelial layer which is transparent. That portion of the palpebral conjunctiva which lines the upper eyelid 28 and the underlying portion of the bulbar conjunctiva defines the upper sac 32 and that portion of the palpebral conjunctiva which lines the lower eyelid 29 and the underlying portion of the bulbar conjunctiva defines the lower sac 33. Upper and lower eyelashes are indicated as 34 and 35 respectively.

A bioerodible ocular insert 10 made in accordance with this invention, is shown in broken lines in operative position in the lower sac 33 of the eye. Ocular insert 10 consists of a bioerodible polymer 12 comprising a continuous matrix having particles of drug dispersed therethrough. When ocular insert 10 is placed in the environment of the eye, polymer 12 gradually bioerodes and releases drug to the eye and surrounding tissue.

The ocular insert 10 as illustrated in FIGS. 11a and 11b can be fabricated in any convenient shape for comfortable retention in the upper sac or lower sac of the eye. The marginal outline of insert 10 can be ellipsoid, donut-shaped, bean-shaped, banana-shaped, circular, square, rectangular, etc. In cross-section, insert 10 can be doubly convex, concavo-convex, rectangular, and the like. Dimensions of the insert can vary widely. The lower limit on the size of the device is governed by the amount of the particular drug to be supplied to the eye and surrounding tissues to elicit the desired pharmacologic response, as well as by the smallest sized device which conveniently can be inserted in the eye. The upper limit on the size of the device is governed by the geometric space limitations in the eye, consistent with comfortable retention of the ocular insert. Satisfactory results can be obtained with an ocular device for insertion in the sac of the eye of from 4 to 20 millimeters in length, 1 to 12 millimeters in width, and 0.1 to 2 millimeters in thickness. Exemplary shapes of inserts include an 8 mm disc, and a 6 mm by 12 mm ellipsoid, each punched out of a 0.4 mm thick drug-containing polymer sheet. The drug-containing polymer sheet was prepared by dissolving both the drug and the polymer in a dry solvent, benzene or 1,4-dioxane and the mixture lyophilized; then the dry mixture was pressed at 100° C and 15,000 psi to give the drug-containing polymer sheet. Ocular inserts prepared by this procedure include 10% pilocarpine nitrate and poly(2,2-dioxo-trans-1,4-cyclohexane dimethylene tetrahydrofuran); 5% pilocarpine free base and poly(2,2-dioxo-trans-1,4-cyclohexane dimethylene tetrahydroduran); 10% hydrocortisone alcohol and poly(2,2-dioxo-trans-1,4-cyclohexane dimethylene tetrahydrofuran); 10% idoxuridine and poly(2,2-dioxo-trans-1,4-cyclohexane dimethylene tetrahydrofuran-2,2-dioxo-oxadimethylene-tetrahydrofuran); and 10% chloramphenicol and poly(2,2-dioxo-trans-1,4-cyclohexane dimethylene tetrahydrofuran-2,2-dioxo-oxadimethylene-tetrahydrofuran). These ocular inserts continuously bioerode and dispense a metered amount of ophthalmic drug or a combination of drug to the eye and its surrounding tissue over a period of time.

Additional ocular devices comprising zinc bacitracin and the random copolymer poly(2,2-dioxo-trans-1,4-cyclohexane dimethylene tetrahydrofuran-2,2-dioxo-1,6-hexamethylene tetrahydrofuran) were prepared by mixing and dispersing at 120° C for 5 minutes the bacitracin into the hot melt of the polymer. After cooling to room temperature, the drug polymer formulation was pressed into a film at 120° C under 10,000 psi for 5 minutes; and then it was templated into ocular devices. The release rate for 3 day ocular devices made from the above drug-polymer formulation is set forth in Table 3 below:

Table 3

| Dimension and Shape | Surface area (cm²) | Zn bacitracin content (mg) | µg/hr for 72 hrs |
|---|---|---|---|
| 6 mm circular | 0.56 | 1.5 | 21 |

Table 3-continued

| Dimension and Shape | Surface area (cm²) | Zn bacitracin content (mg) | μg/hr for 72 hrs |
|---|---|---|---|
| 5 × 8 mm ellipse | 0.62 | 1.6 | 22 |
| 5.6 × 12.7 mm ellipse | 1.1 | 2.9 | 40 |

Figure 12:
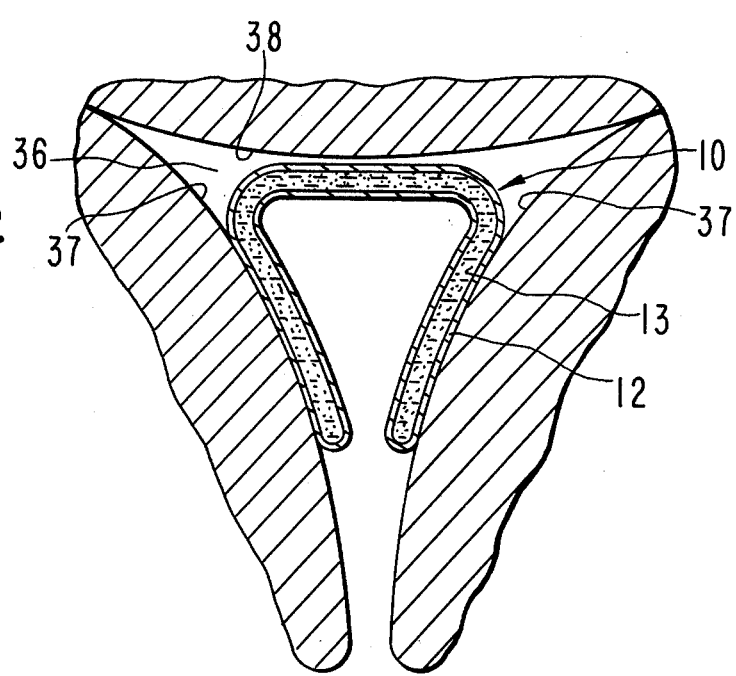

In FIG. 12, there is graphically illustrated a device 10 for releasing a drug 13 within a uterus 36 having sides 37 and a fundus uteri 38. Device 10 as shown in cross-section, is a bioerodible intrauterine device having a round tube shaped body made of bioerodible polymer 12 that contains drug 13 for release in uterus 36 concurrently with the bioerosion of polymer 12. Intrauterine device 10 can have different shapes and dimensions, and these can vary consistent with comfortable placement and effective drug release, in uterus 36. In one application, device 10 is useful for releasing an active agent to the uterus by controlled bioerosion in situ. Device 10 can deliver drugs for inducing uterine contractions for example, oxytocin, ergot alkaloids such as ergonovine and methylergonomine, quinine, quinidine, histamine and sparteine; and the prostaglandins; especially, PGE and $PGF_{2\alpha}$.

The polymers prepared according to the invention are used for coating beneficial agents by known techniques. In one embodiment, slow release fertilizers are made by coating fertilizers in conventional forms such as granules, powders and beads with one of the degradable polymers of the invention. For example, a coated fertilizer is prepared by mixing the polymer and the fertilizer in granular form in a fluidized bed having a conical bottom until an acceptable coat is applied to the fertilizer. The bed is equipped with an air inlet at the top for mixing the polymer and fertilizer until the fertilizer is coated with 1 to 10% by weight of polymer. The temperature of the air is dependent on the concentration of the dispersion, usually 20° to 125° C. In another embodiment, the fertilizer is coated by mixing the polymer with an organic solvent to facilitate its application onto the fertilizer. For example, a slow release urea-based fertilizer is prepared by dissolving the polymer poly(1,4-cyclohexane dicarbinyl-2,2-dioxytetrahydrofuran) in benzene and mixing therein the granules. Next, the solvent is evaporated to yield the coated, slow release fertilizer. The coating composition can additionally contain pigments, dyes, driers and stabilizers. The polymers of the invention also can be used for coating medicines for entering the digestive tract wherein the therapeutic value of the medicine is obtained.

It will be appreciated by those versed in the art, the present invention makes available novel polymers useful for making items of science and commerce including devices for dispensing a beneficial agent. Also, it will be understood by those knowledgeable in the art, that many embodiments of this invention can be made without departing from the spirit and scope of the invention, and the invention is not to be construed as limited, as it embraces all equivalents inherent therein.

We claim:

1. A drug delivery device for the controlled and continuous administration of drug, wherein the device comprises: (a) a shaped matrix sized and adapted for administering drug to an animal and formed of a bioerodible drug release rate controlling pharmaceutically acceptable material, which material comprises a polymer of the formula:

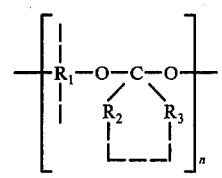

wherein $R_1$ is a member selected from the group of divalent, trivalent and tetravalent radicals consisting of alkylene of 1 to 10 carbons; alkenylene of 2 to 10 carbons; alkyleneoxy of 2 to 6 carbons; cycloalkylene of 3 to 7 carbons; cycloalkylene of 3 to 7 carbons substituted with an alkyl of 1 to 7 carbons, alkoxy of 1 to 7 carbons, an alkylene of 1 to 10 carbons, and an alkenyl of 2 to 7 carbons; cycloalkenylene of 4 to 7 carbons; cycloalkenylene of 4 to 7 carbons substituted with an alkyl of 1 to 7 carbons, an alkoxy of 1 to 7 carbons, an alkylene of 1 to 10 carbons, and an alkenyl of 2 to 7 carbons; arylene; and arylene substituted with an alkyl of 1 to 7 carbons, an alkoxy of 1 to 7 carbons, and an alkenyl of 2 to 7 carbons; $R_2$ and $R_3$ are selected from the group consisting of alkyl of 1 to 7 carbons; alkenyl of 2 to 7 carbons; alkoxy of 1 to 7 carbons; alkenyloxy of 2 to 7 carbons; alkylene of 2 to 6 carbons; alkenylene of 3 to 6 carbons; alkyleneoxy of 2 to 6 carbons; alkenyleneoxy of 3 to 6 carbons; aryloxy; aralkyleneoxy of 8 to 12 carbons; aralkenyleneoxy of 8 to 12 carbons; oxa; $OR_1O$ with $R_1$ as defined above; a heterocyclic ring of 5 to 8 carbon and oxygen atoms formed when $R_2$ and $R_3$ are taken together; a heterocyclic ring of 5 to 8 carbon and oxygen atoms substituted with an alkyl of 1 to 7 carbons, an alkoxy of 1 to 7 carbons and an alkenyl of 2 to 7 carbons formed when $R_2$ and $R_3$ are taken together; a fused polycyclic ring of 8 to 12 carbon and oxygen atoms formed when $R_2$ and $R_3$ are taken together; a fused polycyclic ring of 8 to 12 carbon and oxygen atoms substituted with an alkyl of 1 to 7 carbons, an alkoxy of 1 to 7 carbons and an alkenyl of 2 to 7 carbons; and wherein at least one of said $R_2$ and $R_3$ is a member selected from the group consisting of alkoxy, alkenyloxy and $OR_1O$; $R_2$ and $R_3$ when taken together are a member selected from the group of heterocyclic and fused polycyclic rings having at least one oxygen atom in the ring; and wherein $n$ is greater than 10; (b) a drug selected from the group consisting of locally and systemically acting pharmaceutically acceptable drugs present in the matrix; and, (c) wherein the device when in operation bioerodes at a controlled and continuous rate over a prolonged period of time, thereby administering a therapeutically effective amount of drug to the animal at a controlled and continuous rate over a prolonged period of time.

2. The drug delivery device for the administration of drug according to claim 1 wherein a layer formed of a drug impervious material is suitably fixed to the matrix.

3. The drug delivery device for the administration of drug according to claim 1 wherein the matrix has a passageway for increasing the surface releasing drug from the device over a prolonged period of time.

4. The drug delivery device for the administration of drug according to claim 1 wherein the matrix comprises intertwisted fibers thereby providing means for influencing the rate of drug release throughout the drug release period.

5. The drug delivery device for the administration of drug according to claim 1 wherein the device comprises a continuous matrix having drug dispersed therethrough and wherein the matrix has a geometric shape sized and adapted for placement on the animal and implantation and insertion in the animal.

6. The drug delivery device for the administration of drug according to claim 1 wherein the matrix is a wall forming a tube-shaped body containing drug therein which drug is released by controlled bioerosion over a prolonged period of time.

7. The drug delivery device for administering drug at a controlled rate over a prolonged period of time according to claim 1 wherein the device is sized, shaped and adapted for releasing drug in the vagina.

8. The drug delivery device for administering drug at a controlled rate over a prolonged period of time according to claim 1 wherein the device is sized, shaped and adapted for use as an implant.

9. The drug delivery device for administering drug at a controlled rate over a prolonged period of time according to claim 1 wherein the device is sized, shaped and adapted for releasing drug in the gastrointestinal tract.

10. The drug delivery device for administering drug at a controlled rate over a prolonged period of time according to claim 1 wherein the device is sized, shaped and adapted for releasing drug in the anus.

11. The drug delivery device for administering drug at a controlled rate over a prolonged period of time according to claim 1 wherein the device is sized, shaped and adapted for releasing drug in the uterus.

12. The drug delivery device for administering drug at a controlled rate over a prolonged period of time according to claim 1 wherein the device is sized, shaped and adapted for releasing drug intramuscularly.

13. The drug delivery device for administering drug at a controlled rate over a prolonged period of time according to claim 1 wherein the device is sized, shaped and adapted for releasing drug subcutaneously.

14. The drug delivery device for administering drug at a controlled rate over a prolonged period of time according to claim 1 wherein the device is sized, shaped and adapted for releasing drug in the eye.

15. The drug delivery device for administering drug at a controlled rate over a prolonged period of time according to claim 1 wherein the device is manufactured as an ocular insert sized, shaped and adapted for placement in the eye, with the insert formed of drug release rate controlling material containing drug, and which material has a drug impervious layer on a surface thereof.

16. The drug delivery device for administering drug at a controlled rate over a prolonged period of time according to claim 1 wherein the device is sized, shaped and adapted for releasing drug to the skin.

17. The drug delivery device for administering drug at a controlled rate over a prolonged period of time according to claim 1 wherein the drug is a member selected from the group consisting of androgenic, estrogenic, and progestational steroids.

18. The drug delivery device for administering drug at a controlled rate over a prolonged period of time according to claim 1 wherein the drug is a member selected from the group consisting of 17α-hydroxy-progesterone, 19-nor-progesterone, progesterone and norethindrone.

19. The drug delivery device for administering an effective amount of drug at a controlled rate over a prolonged period of time according to claim 1 wherein the device is sized and shaped as an implant formed of poly(2,2-dioxo-cis/trans-1,4-cyclohexane dimethylene tetrahydrofuran) containing norethindrone.

20. The drug delivery device for administering drug at a controlled rate over a prolonged period of time according to claim 1 wherein the device is sized and shaped as an implant adapted for administering drug to a human, and wherein the implant is formed of poly(2,2-dioxo-trans-1,4-cyclohexane dimethylene tetrahydrofuran) and the drug is hormonal 17-hydroxy-19-nor-17α-pregn-4-en-20-yn-3-one useful as a fertility inhibitor.

21. The drug delivery device for the administration of drug according to claim 1 wherein $R_1$ is divalent, $R_2$ and $R_3$ are taken together to form a heterocyclic ring with $R_2$ a member selected from the group consisting of alkyleneoxy and alkenyleneoxy, and $R_3$ is a member selected from the group consisting of alkyleneoxy, alkenyleneoxy and alkylene.

22. The drug delivery device for administering drug at a controlled rate over a prolonged period of time wherein the locally and systemically acting drug according to claim 1 is a member selected from the group consisting of physiologically and pharmacologically effective central nervous system drugs, hypnotic, sedative, psychic energizer, tranquilizer, anticonvulsant, antiparkinson, muscle relaxant, analgesic, antipyretic, anti-inflammatory, anesthetic, antispasmodic, antimicrobial, antiviral, antiulcer, hormonal, sympathomimetic, diuretic, hypoglycemic, vitamin and opthalmic drug which drug is released in a therapeutically effective amount as the device bioerodes over a prolonged period of time.

23. The drug delivery device for the administration of an antimicrobial drug according to claim 1 wherein the device is formed of poly(2,2-dioxo-1,6-hexamethylene tetrahydrofuran) and wherein the device is adapted for application to the skin by inunction.

24. The drug delivery device for administering drug according to claim 1 wherein the matrix and drug form an ointment for topical application to skin, mucosa and wounds, and wherein the polymer is viscous poly(2,2-dioxo-1,6-hexamethylene tetrahydrofuran) and the drug is sulfonamide.

25. The drug delivery device for administering drug according to claim 1 wherein the device is adapted for application to skin, mucosa and wounds, and wherein the device comprises an ointment and a support layer with the layer made of a non-toxic material, and wherein the ointment is formed of matrix and drug, which matrix is viscous poly(2,2-dioxo-1,6-hexamethylene tetrahydrofuran) and which drug is sulfonamide.

26. A drug delivery device for the controlled administration of drug, wherein the device comprises: (a) a shaped matrix sized and adapted for administering drug to a human and formed of a hydrophobic, bioerodible drug release rate controlling material, which material comprises a polymer of the formula:

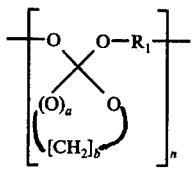

wherein $R_1$ is a member selected from the group consisting of alkylene of 1 to 10 carbons; alkenylene of 2 to 10 carbons; alkyleneoxy of 2 to 6 carbons; cycloakylene of 3 to 7 carbons; cycloalkylene of 3 to 7 carbons substituted with a member selected from the group consisting of an alkyl of 1 to 7 carbons, an alkoxy of 1 to 7 carbons, alkylene of 1 to 10 carbons, and an alkenyl of 2 to 7 carbons, cycloalkenylene of 4 to 7 carbons, cycloalkenylene of 4 to 7 carbons substituted with an alkyl of 1 to 7 carbons, an alkoxy of 1 to 7 carbons and an alkenyl of 2 to 7 carbons; arylene; and arylene substituted with an alkyl of 1 to 7 carbons, an alkoxy of 1 to 7 carbons and an alkenyl of 2 to 7 carbons; and wherein $a$ is 0 or 1, $b$ is 2 to 6, and $n$ is greater than 10; (b) a drug selected from the group consisting of physiologically and pharmacologically active drugs present in the matrix; and (c) wherein the device when in operation bioerodes and releases drug at a rate preselected from (1) a zero order rate, (2) a continuous rate and (c) a variable rate, which rate is produced by preselecting the polymer, the drug and the geometric shape of the device.

27. A drug delivery device for the controlled and continuous administration of drug according to claim 1, wherein the matrix is poly(2,2-dioxo-cis/trans-1,4-cyclohexane dimethylene tetrahydrofuran).

28. A drug delivery device for the controlled and continuous administration of drug according to claim 1, wherein the matrix is poly(2,2-dioxo-trans-1,4-cyclohexane dimethylene tetrahydrofuran).

29. A method for the controlled administration of a drug to an animal which method comprises administering the drug delivery device according to claim 1 to the animal.

30. A method for the controlled administration of a drug to an animal which method comprises administering the drug delivery device according to claim 1, wherein the animal is a mammal, the device is sized, shaped and adapted for implantation in the mammal, and the drug in the device is a member selected from the group consisting of estrogenic and progestational steroids.

31. The method for the controlled administration of drug according to claim 29, wherein the animal is a human.

* * * * *